United States Patent
Duncan et al.

(10) Patent No.: US 9,121,033 B2
(45) Date of Patent: Sep. 1, 2015

(54) POLYNUCLEOTIDES ENCODING TREHALOSE-6-PHOSPHATE PHOSPHATASE AND METHODS OF USE THEREOF

(75) Inventors: Kateri Duncan, West Des Moines, IA (US); Michael L. Nuccio, Research Triangle Park, NC (US); Weining Gu, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 330 days.

(21) Appl. No.: 13/549,794

(22) Filed: Jul. 16, 2012

(65) Prior Publication Data

US 2013/0019342 A1    Jan. 17, 2013

Related U.S. Application Data

(60) Provisional application No. 61/508,605, filed on Jul. 15, 2011, provisional application No. 61/522,549, filed on Aug. 11, 2011.

(51) Int. Cl.
| | |
|---|---|
| *C12N 15/82* | (2006.01) |
| *C07H 21/04* | (2006.01) |
| *C12N 5/04* | (2006.01) |
| *C12N 15/00* | (2006.01) |
| *C12N 9/16* | (2006.01) |
| *C12Q 1/68* | (2006.01) |

(52) U.S. Cl.
CPC .............. *C12N 15/8273* (2013.01); *C12N 9/16* (2013.01); *C12Q 1/6895* (2013.01); *C12Y 204/01216* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 8,129,588 B2* | 3/2012 | Nuccio et al. ................. 800/287 |
| 2008/0148432 A1 | 6/2008 | Abad |
| 2014/0143908 A1* | 5/2014 | Basu et al. .................... 800/289 |

FOREIGN PATENT DOCUMENTS

| WO | 2005/102034 | 11/2005 |
| WO | 2005102034 | 11/2005 |
| WO | 2008/071767 | 6/2008 |

OTHER PUBLICATIONS

Pramanik et al, 2005, Plant Mol. Bio., 58:751-762.*
Krasensky et al, 2014, Antioxidants & Redox Sig., 21:1289-1304.*
Van Houtte et al, 2013, Plant Sig. & Behavior, 8:e23209-1-e23209-5.*
Habibur Rahman Pramanik et al., "Functinoal Identification of a Trehalose 6-phosphate Phosphatase Gene that is Involved in Transient Induction of Trehalose Biosynthesis during Chilling Stress in Rice," Plant Molecular Biology, Kluwer Academic Publishers, Dordrecht, NL, 58(6), Aug. 1, 2005, pp. 751-762.
Garg et al., "Trehalose accumulation in rice plants confers high tolerance levels to different abiotic stresses," Proceedings of the Natinoal Academy of Sciences, Natinoal Academy of Sciences, US, Dec. 10, 2002, 99(25), pp. 15898-15903.
International Search Report dated Nov. 7, 2012 for International Patent Application No. PCT/US2012/046341.
International Search Report, Written Opinion dated Jan. 30, 2013 and International Preliminary Report on Patentability for International Patent Application No. PCT/US2012/046888.

* cited by examiner

*Primary Examiner* — David H Kruse
*Assistant Examiner* — Jason Deveau Rosen
(74) *Attorney, Agent, or Firm* — Karen Moon Bruce

(57) ABSTRACT

The present invention relates generally to the field of molecular biology and regards various polynucleotides, polypeptides and methods that may be employed to enhance yield in transgenic plants. Specifically the transgenic plants may exhibit any one of the traits consisting of increased yield, increased tolerance to abiotic stress, increased cell growth and increased nutrient use efficiency.

11 Claims, No Drawings

ABSTRACT

SEQUENCE LISTING

<160> NUMBER OF SEQ ID NOS: 15

<210> SEQ ID NO 1
<211> LENGTH: 1116
<212> TYPE: DNA
<213> ORGANISM: Oryza sativa

<400> SEQUENCE: 1

| | |
|---|---|
| atggatttga gcaatagctc acctgtcatc accgatccgg tggcgatcag ccagcagttg | 60 |
| ttgggcggcc tgccttcaaa tctgatgcag ttttcagtca tgcccggtgg ctactccagc | 120 |
| tctggcatga acgttggtgt cagtaggctc aaaatcgagg aagtccttgt caatggactg | 180 |
| cttgatgcca tgaaatcctc gtcacctcgc aggaggctga atgtagcatt tggcgaggac | 240 |
| aattcatctg aagaagaaga ccctgcttac agcgcttgga tggcaaaatg tccttctgct | 300 |
| ttggcttcct tcaagcaaat tgtagccagt gcacaaggga agaagattgc tgtgtttcta | 360 |
| gactatgacg gcacactgtc gcctattgtg atgatcctg acaaagcagt gatgtctccc | 420 |
| gtgatgagag ctgctgtgag aaatgttgcg aagtacttcc ccactgcaat tgtcagcgga | 480 |
| aggtcccgca ataaggtgtt tgaatttgta aaactgaagg agctttatta tgctggaagt | 540 |
| catggtatgg acataatggc accttcagca atcatgagc acagtgctga aagagcaaa | 600 |
| caggccaatc tcttccaacc tgcacacgac tttctgccaa tgatcgatga ggttaccaag | 660 |
| tccctcttgc aagttgtcag tggaattgaa ggtgcaactg ttgagaacaa caaattctgc | 720 |
| gtttctgtac attatcgcaa cgttgcagag aaggattgga aactggtcgc acggctcgta | 780 |
| aacgaagtgc tggaggcttt tcctcgtctc aaagtaacca atggacgaat ggttttagag | 840 |
| gttcgtccgg tgatcgactg ggacaaggga aaggctgtgg agtttctgct ccagtcactc | 900 |
| gggctaaatg actctgaaaa tgtgatcccc atctacattg agacgacag aactgacgaa | 960 |
| gacgctttca aggtacttcg acagcgaaat tgcggttatg aatactagt ttcacaggtt | 1020 |
| cccaaggaaa ctgaagcctt ctactcgctg agagatccat ctgaagtgat ggagttcctc | 1080 |
| aatttcttgg tgagatggaa gaagcactca gtgtga | 1116 |

<210> SEQ ID NO 2
<211> LENGTH: 371
<212> TYPE: PRT
<213> ORGANISM: Oryza sativa

<400> SEQUENCE: 2

Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Gly Met Asn Val Gly Val Ser
        35                  40                  45

Arg Leu Lys Ile Glu Glu Val Leu Val Asn Gly Leu Leu Asp Ala Met
    50                  55                  60

Lys Ser Ser Ser Pro Arg Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95

Cys Pro Ser Ala Leu Ala Ser Phe Lys Gln Ile Val Ala Ser Ala Gln
            100                 105                 110

Gly Lys Lys Ile Ala Val Phe Leu Asp Tyr Asp Gly Thr Leu Ser Pro
        115                 120                 125

```
Ile Val Asp Asp Pro Asp Lys Ala Val Met Ser Pro Val Met Arg Ala
130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
210                 215                 220

Val Val Ser Gly Ile Glu Gly Ala Thr Val Glu Asn Asn Lys Phe Cys
225                 230                 235                 240

Val Ser Val His Tyr Arg Asn Val Ala Glu Lys Asp Trp Lys Leu Val
                245                 250                 255

Ala Arg Leu Val Asn Glu Val Leu Glu Ala Phe Pro Arg Leu Lys Val
            260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
290                 295                 300

Ser Glu Asn Val Ile Pro Ile Tyr Ile Gly Asp Asp Arg Thr Asp Glu
305                 310                 315                 320

Asp Ala Phe Lys Val Leu Arg Gln Arg Asn Cys Gly Tyr Gly Ile Leu
                325                 330                 335

Val Ser Gln Val Pro Lys Glu Thr Glu Ala Phe Tyr Ser Leu Arg Asp
            340                 345                 350

Pro Ser Glu Val Met Glu Phe Leu Asn Phe Leu Val Arg Trp Lys Lys
        355                 360                 365

His Ser Val
    370

<210> SEQ ID NO 3
<211> LENGTH: 1113
<212> TYPE: DNA
<213> ORGANISM: Oryza sativa

<400> SEQUENCE: 3
atggatctga gcaacagcag cccggtgatt accgatccgg tggcgattag ccagcagctg      60
ctgggcggcc tgccgagcaa cctgatgcag tttagcgtga tgccgggcgg ctatagcagc     120
agcggcatga acgtgggcgt gagccgcctg aaaattgaag aagtgctggt gaacggcctg     180
ctggatgcga tgaaaagcag cagcccgcgc cgccgcctga acgtggcgtt tggcgaagat     240
aacagcagcg aagaagaaga tccggcgtat agcgcgtgga tggcgaaatg cccgagcgcg     300
ctggcgagct ttaaacagat tgtggcgagc gcgcagggca aaaaaattgc ggtgtttctg     360
gattatgatg gcaccctgag cccgattgtg gatgatccgg ataaagcggt gatgagcccg     420
gtgatgcgcg cggcggtgcg caacgtggcg aaatattttc cgaccgcgat tgtgagcggc     480
cgcagccgca acaaagtgtt tgaatttgtg aaactgaaag aactgtatta tgcgggcagc     540
catggcatgg atattatggc gccgagcgcg aaccatgaac atagcgcgga aaaaagcaaa     600
caggcgaacc tgtttcagcc ggcgcatgat tttctgccga tgattgatga agtgaccaaa     660
agcctgctgc aggtggtgag cggcattgaa ggcgcgaccg tggaaaacaa caaatttttgc    720
```

```
gtgagcgtgg attatcgcaa cgtggcggaa aaagattgga aactggtggc gcgcctggtg      780
aacgaagtgc tggaagcgtt tccgcgcctg aaagtgacca acggccgcat ggtgctggaa      840
gtgcgcccgg tgattgattg ggataaaggc aaagcggtgg aatttctgct gcagagcctg      900
ggcctgaacg atagcgaaaa cgtgattccg atttatattg gcgatgatcg caccgatgaa      960
gatgcgttta aagtgctgcg ccagcgcaac tgcggctatg cattctggt gagccaggtg      1020 ccgaaagaaa ccgaagcgtt ttatagcctg cgcgatccga gcgaagtgat ggaatttctg     1080
aactttctgg tgcgctggaa aaaacatagc gtg                                  1113
```

```
<210> SEQ ID NO 4
<211> LENGTH: 371
<212> TYPE: PRT
<213> ORGANISM: Oryza sativa

<400> SEQUENCE: 4
```

| | | | | | | | | | | | | | | |
|---|---|---|---|---|---|---|---|---|---|---|---|---|---|---|
| Met | Asp | Leu | Ser | Asn | Ser | Ser | Pro | Val | Ile | Thr | Asp | Pro | Val | Ala | Ile |
| 1 | | | | 5 | | | | | 10 | | | | | 15 | |

Ser Gln Gln Leu Leu Gly Gly Leu Pro Ser Asn Leu Met Gln Phe Ser
                20                  25                  30

Val Met Pro Gly Gly Tyr Ser Ser Gly Met Asn Val Gly Val Ser
            35                  40                  45

Arg Leu Lys Ile Glu Glu Val Leu Val Asn Gly Leu Leu Asp Ala Met
    50                  55                  60

Lys Ser Ser Ser Pro Arg Arg Arg Leu Asn Val Ala Phe Gly Glu Asp
65                  70                  75                  80

Asn Ser Ser Glu Glu Glu Asp Pro Ala Tyr Ser Ala Trp Met Ala Lys
                85                  90                  95

Cys Pro Ser Ala Leu Ala Ser Phe Lys Gln Ile Val Ala Ser Ala Gln
            100                 105                 110

Gly Lys Lys Ile Ala Val Phe Leu Asp Tyr Asp Gly Thr Leu Ser Pro
        115                 120                 125

Ile Val Asp Asp Pro Asp Lys Ala Val Met Ser Pro Val Met Arg Ala
    130                 135                 140

Ala Val Arg Asn Val Ala Lys Tyr Phe Pro Thr Ala Ile Val Ser Gly
145                 150                 155                 160

Arg Ser Arg Asn Lys Val Phe Glu Phe Val Lys Leu Lys Glu Leu Tyr
                165                 170                 175

Tyr Ala Gly Ser His Gly Met Asp Ile Met Ala Pro Ser Ala Asn His
            180                 185                 190

Glu His Ser Ala Glu Lys Ser Lys Gln Ala Asn Leu Phe Gln Pro Ala
        195                 200                 205

His Asp Phe Leu Pro Met Ile Asp Glu Val Thr Lys Ser Leu Leu Gln
    210                 215                 220

Val Val Ser Gly Ile Glu Gly Ala Thr Val Glu Asn Asn Lys Phe Cys
225                 230                 235                 240

Val Ser Val Asp Tyr Arg Asn Val Ala Glu Lys Asp Trp Lys Leu Val
                245                 250                 255

Ala Arg Leu Val Asn Glu Val Leu Glu Ala Phe Pro Arg Leu Lys Val
            260                 265                 270

Thr Asn Gly Arg Met Val Leu Glu Val Arg Pro Val Ile Asp Trp Asp
        275                 280                 285

Lys Gly Lys Ala Val Glu Phe Leu Leu Gln Ser Leu Gly Leu Asn Asp
    290                 295                 300

```
Ser Glu Asn Val Ile Pro Ile Tyr Ile Gly Asp Arg Thr Asp Glu
305                 310                 315                 320

Asp Ala Phe Lys Val Leu Arg Gln Arg Asn Cys Gly Tyr Gly Ile Leu
            325                 330                 335

Val Ser Gln Val Pro Lys Glu Thr Glu Ala Phe Tyr Ser Leu Arg Asp
        340                 345                 350

Pro Ser Glu Val Met Glu Phe Leu Asn Phe Leu Val Arg Trp Lys Lys
    355                 360                 365

His Ser Val
    370

<210> SEQ ID NO 5
<211> LENGTH: 1113
<212> TYPE: DNA
<213> ORGANISM: Oryza sativa

<400> SEQUENCE: 5
atggatctga gcaacagcag cccggtgatt accgatccgg tggcgattag ccagcagctg      60
ctgggcggcc tgccgagcaa cctgatgcag tttagcgtga tgccgggcgg ctatagcagc     120
agcggcatga cgtgggcgt gagccgcctg aaaattgaag aagtgctggt gaacggcctg     180
ctggatgcga tgaaaagcag cagcccgcgc cgccgcctga acgtggcgtt tggcgaagat     240
aacagcagcg aagaagaaga tccggcgtat agcgcgtgga tggcgaaatg cccgagcgcg     300
ctggtgagct ttaaacagat tgtggcgagc gcgcagggca aaaaaattgc ggtgtttctg     360
gattatgatg gcacccctgag cccgtttgtg gatgatccgg ataaagcggt gatgagcccg     420
gtgatgcgcg cggcggtgcg caacgtggcg aaatattttc cgaccgcgat tgtgagcggc     480
cgcagccgca caaagtgtt tgaatttgtg aaactgaaag aactgtatta tgcgggcagc     540
catggcatgg atattatggc gccgagcgcg aaccatgaac atagcgcgga aaaaagcaaa     600
caggcgaacc tgtttcagcc ggcgcatgat tttctgccga tgattgatga agtgaccaaa     660
agcctgctgc aggtggtgag cggcattgaa ggcgcgaccg tggaaaacaa caatttttgc     720
gtgagcgtgc attatcgcaa cgtggcggaa aaagattgga actggtggc gcgcctggtg     780 aacgaagtgc tggaagcgtt tccgcgcctg aaagtgacca acggccgcat ggtgctggaa     840
gtgcgcccgg tgattgattg gataaaggc aaagcggtgg aatttctgct gcagagcctg     900
ggcctgaacg atagcgaaaa cgtgattccg atttatattg gcgatgatcg caccgatgaa     960
gatgcgttta agtgctgcg ccagcgcaac tgcggctatg gcattctggt gagccaggtg    1020
ccgaaagaaa ccgaagcgtt ttatagcctg cgcgatccga gcgaagtgat ggaatttctg    1080
aactttctgg tgcgctggaa aaaacatagc gtg                                  1113

<210> SEQ ID NO 6
<211> LENGTH: 371
<212> TYPE: PRT
<213> ORGANISM: Oryza sativa

<400> SEQUENCE: 6

Met Asp Leu Ser Asn Ser Ser Pro Val Ile Thr Asp Pro Val Ala Ile
1               5                   10                  15

Ser Gln Gln Leu Leu Gly Gly Leu Pro Ser Asn Leu Met Gln Phe Ser
            20                  25                  30

Val Met Pro Gly Gly Tyr Ser Ser Gly Met Asn Val Gly Val Ser
        35                  40                  45
```

```
Arg Leu Lys Ile Glu Glu Val Leu Val Asn Gly Leu Leu Asp Ala Met
 50                  55                  60
Lys Ser Ser Pro Arg Arg Leu Asn Val Ala Phe Gly Glu Asp
 65                  70                  75                  80
Asn Ser Ser Glu Glu Glu Asp Pro Ala Tyr Ser Ala Trp Met Ala Lys
                 85                  90                  95
Cys Pro Ser Ala Leu Val Ser Phe Lys Gln Ile Val Ala Ser Ala Gln
            100                 105                 110
Gly Lys Lys Ile Ala Val Phe Leu Asp Tyr Asp Gly Thr Leu Ser Pro
        115                 120                 125
Phe Val Asp Asp Pro Asp Lys Ala Val Met Ser Pro Val Met Arg Ala
130                 135                 140
Ala Val Arg Asn Val Ala Lys Tyr Phe Pro Thr Ala Ile Val Ser Gly
145                 150                 155                 160
Arg Ser Arg Asn Lys Val Phe Glu Phe Val Lys Leu Lys Glu Leu Tyr
                165                 170                 175
Tyr Ala Gly Ser His Gly Met Asp Ile Met Ala Pro Ser Ala Asn His
            180                 185                 190
Glu His Ser Ala Glu Lys Ser Lys Gln Ala Asn Leu Phe Gln Pro Ala
        195                 200                 205
His Asp Phe Leu Pro Met Ile Asp Glu Val Thr Lys Ser Leu Leu Gln
210                 215                 220
Val Val Ser Gly Ile Glu Gly Ala Thr Val Glu Asn Asn Lys Phe Cys
225                 230                 235                 240
Val Ser Val His Tyr Arg Asn Val Ala Glu Lys Asp Trp Lys Leu Val
                245                 250                 255
Ala Arg Leu Val Asn Glu Val Leu Glu Ala Phe Pro Arg Leu Lys Val
            260                 265                 270
Thr Asn Gly Arg Met Val Leu Glu Val Arg Pro Val Ile Asp Trp Asp
        275                 280                 285
Lys Gly Lys Ala Val Glu Phe Leu Leu Gln Ser Leu Gly Leu Asn Asp
290                 295                 300
Ser Glu Asn Val Ile Pro Ile Tyr Ile Gly Asp Asp Arg Thr Asp Glu
305                 310                 315                 320
Asp Ala Phe Lys Val Leu Arg Gln Arg Asn Cys Gly Tyr Gly Ile Leu
                325                 330                 335
Val Ser Gln Val Pro Lys Glu Thr Glu Ala Phe Tyr Ser Leu Arg Asp
            340                 345                 350
Pro Ser Glu Val Met Glu Phe Leu Asn Phe Leu Val Arg Trp Lys Lys
        355                 360                 365
His Ser Val
        370

<210> SEQ ID NO 7
<211> LENGTH: 208
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
```

```
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (110)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (147)..(148)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (176)..(196)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid

<400> SEQUENCE: 7

Lys Xaa Xaa Xaa Xaa Xaa Val Leu Phe Gln Pro Ala Ser Glu Phe
 1               5                  10                  15

Leu Pro Met Ile Asp Glu Val Tyr Lys Xaa Leu Val Glu Lys Thr Lys
                20                  25                  30

Xaa Xaa Ile Pro Gly Ala Lys Val Glu Asn Asn Lys Phe Cys Val Ser
            35                  40                  45

Val His Phe Arg Cys Val Asp Glu Lys Xaa Trp Xaa Xaa Leu Ala Xaa
        50                  55                  60

Xaa Val Arg Ser Val Leu Lys Glu Tyr Pro Lys Leu Arg Leu Thr Gln
65                  70                  75                  80

Gly Arg Lys Val Leu Glu Ile Arg Pro Xaa Ile Lys Trp Asp Lys Gly
                85                  90                  95

Lys Ala Leu Glu Phe Leu Leu Glu Ser Leu Gly Phe Ala Xaa Xaa Xaa
                100                 105                 110
```

```
Xaa Xaa Xaa Xaa Xaa Asn Xaa Xaa Asp Val Leu Pro Ile Tyr Ile
            115                 120                 125

Gly Asp Asp Arg Thr Asp Glu Asp Ala Phe Lys Val Leu Arg Glu Arg
130                 135                 140

Gly Gln Xaa Xaa Gly Phe Gly Ile Leu Val Ser Lys Xaa Pro Lys Glu
145                 150                 155                 160

Thr Xaa Ala Ser Tyr Ser Leu Gln Asp Pro Ser Glu Val Met Glu Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Phe Leu Xaa Arg Leu Val Xaa Trp Lys Lys Xaa Ser
            195                 200                 205
```

```
<210> SEQ ID NO 8
<211> LENGTH: 19
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 8

Arg Xaa Xaa Ser Trp Val Asp Ser Met Arg Ala Ser Ser Pro Thr Xaa
1               5                   10                  15

Xaa Lys Ser

<210> SEQ ID NO 9
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Gly Asp Asp Arg Thr Xaa Gln Asp Ala Phe
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Consensus Sequence

<400> SEQUENCE: 10

Leu Asp Tyr Asp Gly Thr Leu Ser Pro Ile Val Asp
1               5                   10

<210> SEQ ID NO 11
<211> LENGTH: 4447
<212> TYPE: DNA
<213> ORGANISM: Oryza sativa
```

```
<400> SEQUENCE: 11
cggaccgcta ggacgatggt gtgatgtggg aacacgaaga aaacatgagg aaaaaatatt        60
aaaatgaatt tcccacttaa aatgcatcaa ataaaaaaaa taaagaaacg accgggaata       120
gacacagggt ttgtgaacta gctagggcaa acatcatatg gtcccttgct gatgcacaag       180
tacattgaga tgtcatttca attctgtgca tcatatgcat gtggtccctt gctgaatatt       240
actcttgaaa tatctaccag tgccaatcta ttgcatgact taattaattc acaggttttg       300
ttgattacat tattagtaag cttgagagca caagctcaat ggattttttct ataaatgggg       360 atcattttgc aattttctttt gtcgtgcaaa gttagccttc tttattacta cttctgtttt       420
taaatatacg atcctattga cttttggtca tatatttaac catgtatctt atttagatag       480
tttgcgcaaa tatatatacc ttcaatgata aaattagtta caatgaaaca aatgatattt       540
acgcaattct ttttactaaa caagtcacaa gaagtacctg cagcaatata tgttggaacc       600
gtgcagtaga tcgagcctag ctacgcaaaa aaacaaaaag agaaaaaaag ggaaaggaaa       660
aacattaatc atgcatgagc agtatgcccg gcaactggaa tttgtcaaag atatggggag       720
aggagaataa tacaagtact actactacct agctctacca tgcatatgca cccaaaggca       780
aactggatta ttggataaag cacagatgct ggcaaaacaa tccttaagcc tcccctccct       840
gcttctttat ttttgggcag cctctaccgg acggtgccgt ggtccattgg accagtaggt       900
ggcgacatac atggtttggg ttaagtctag gagagcagtg tgtgtgcgcg cgcaagagag       960
agagactgtg agtctgggag tagccctctc ccctcctttg gccatcttcc tcgtgtatat      1020
gcatatatgc atcatcgcaa cggtgtatat ttgtggtgtg gcgggtgtgg cattggattg      1080
cccccatttt ggctcgtgct tcccagttag ggtaaaacct gtggtaaact tgctagcccc      1140
acgccaaagt taccccttctt tattgttgaa agggagagga ggtgtgtgaa ttgtgatgga      1200
gggagagaga gagagagata gaaagagaga tgtgtgtcaa agcaagcaag aaaccagttt      1260
cacaaagagc tactactagt actagtgtac tactgtggta cagtgcccaa tgtcctttct      1320
ccggactcga ctccactaat attctcctct tctcgcgcgg ctcgttatat tctcgtcatc      1380
attggaggct ttagcaagca agaagagagg cagtggtggt ggtggtggag gaggagctag      1440
ctagcctgtg cttgctgatc ggtgctgagc tgaggaatcg ttcgatcgat cgggcgagtc      1500
gacgagggga agagttgagc tgaggcgcat cgagaacaag atcaacaggc aggtcacctt      1560
ctccaagcgc cgcaacggcc tcctcaagaa ggcctacgag ctgtccgttc tctgcgacgc      1620
cgaggtcgcg ctcatcatct tctccagccg cggcaagctc tacgagttcg gcagcgccgg      1680
gtataattaa tacagacaca acaacacaca caaccaacaa accagcatca atttgaacct      1740
gcagatctgc tgttttctct gatcaattgc ttcttttttt ttgttcttttt ttgtttctttt      1800 tatctgctgc aacggcgtcc tgctcctctg gggtttctcg ttttctttttt catttatttt      1860 tagcaggtgc caagtagccg agctactata cttacctggc catgttaatt attttattcc      1920
gtctgtctgt gtgtgtctgt gcatactact ataggggacat ggcgcggtgt tcttataaac      1980
cgggaggccg gatccctaac tagcatggga ggatatcttt tcagcggatc tatacaaacc      2040
ctactcctgc tgacctcttt cttccagttt tccgggtct tccttggatt attattgccc      2100
atcttccggg ttgtgcgtgt gtcagagaca gctcgaacga taaatttctc aaaaccagta      2160
ctagagaggg tgtgttgtgt gtgagaactg agtggagagt tagcatgaag gctgcaaact      2220
agaaaggaag gtatgttctt tccttttttga tccatcaggg gagcccccttc tggtattaag      2280 atctttccgg cacattgatt ttcatacttt gtgatgaccc tggaagaatc ggcgtagcag      2340
```

```
cgtagcaccg ctccattttg gtcttaccct cacctcccca tgctatgaac tgatcaatttt    2400 cattgttctt catcacccttc tcctagcttt tccacttcct tcggatctca tgccatgttt     2460
ctcagcatga atcaaattta attcgtgttt tctacttcca tatatactgg aagaaattta     2520
attagatcta ttttttgctcg ggaggtcttc atactttgag ttctgatgcc atcaccttat    2580
ttcccccccc cccttctctt gttctatctt cttcctcatc ttggcttgat cattttgatc    2640
tgtcagttat agcatgatgc attctcaatt tgactgtatg taagttcaac cggaaatatg    2700
ttgaatggat tttctatata tcaacacttg atgtcaggcc tgcatctgtt tcgcttgtgg    2760
tggtgtggcc aaaattgtct atatttgatc tttgctcttc tttctcctca tttcatgacg    2820
attcctacta cggcttaaac cattctttat tctttactaa tcatggatgt tgcttgactc    2880
ctagttgttt cgtactagct caacttggag atcttttcat tatttgccta gttggtgggt    2940
acgtttgtga cagatctaaa atggtgcacg aaaagtttta cttattatga aaaagggag    3000 cttaacaggg taatttctct atttattcgt gatgacattt tttccttgat aagggggatt    3060
ttttataatc tgcactcaca tgtttatatg taaaatctag ctcttttgtt ttgttttttgg    3120 catatttccc gctaagtata gagtttatgt ggataacatt ataacttttc aagatccaat    3180
ccacatcttt gattgtgaaa atcatacaat agggaaaatc aactgaaggg ttaattagat    3240
gctatatgca tatatatata tatgtgcgcg cgcgcgcgcc tgaatttaac tatgtatgca    3300
tccaactgtt tcattgaaaa agatttgata ttttcagtc tattctttt cgagtatata    3360 tttaatatgt ttcaatctgt tttgaccatt ataagataaa gcctatattc accaggcatt    3420
tgagatgatc ttttcatgca tgaaaaagct gttgttatca cttcaactaa ccagacgatc    3480
taacatgtat ttgtataaga aacagacctt gatttccttc tgtaaaatca tgcatgtgtt    3540
cgttttgaat tggagtcggc gcgcctgtgt tttgaccgtc aggaaagtct ttttttttccc    3600 tgaatagtca agggtctata cttcttgaag caattgggac actaatcaat tattgtttat    3660
acctcggacc atcttttcct tcttcacacc actaatcagt ttatgccttg gaccattaat    3720
tgtgttgttc acaagcttct tgtttatggt ttacaaagca ttcgcctaga tttgtgtgtg    3780
tctctacaca tcgatcactt ttaaatactt gtcgctttca gttattcttt taacgtttgg    3840
ttatttatct tatttaaaaa aattatcgta ttattattta ttttgtttgt gatttacttt    3900
attatcaaaa gtatttcaaa tatgactttat cttttttttat aagtgcacta atttttcaaa    3960
taagatgaat ggtcaaatgt tacaagaaaa agttaaagca accactaatt tagggcggag    4020
gtagtaaaac ctagttattg taaccaataa ttttatcaat ctataaatgc aacacaaagt    4080
cacttcgtga tatctcacac aaagccactt caacgatgaa agctgactgc atgttttatc    4140
aaaacacatg tgatcagttt gttggatgaa aaaaattatc tatgtcataa atcaagagtt    4200
ataatataag cttctggctc tacaagtaac atttctatgt ttttttttta cgttcttaca    4260
tactatgttt tgccaaaaaa aacatgatca ttttgttgga cgaaaagaaa tagtaaatat    4320
agagtgacct ttgatatcat tataatataa gcttctgcct ctataaataa catctatgca    4380 cttttttacgt cgtagtaatt tgatatatga gaaatttaca tataacatttt ttgtgcagca    4440 taaccac                                                               4447

<210> SEQ ID NO 12
<211> LENGTH: 10
<212> TYPE: PRT
<213> ORGANISM: Artificial Sequence
<220> FEATURE:
<223> OTHER INFORMATION: B-phosphatase box consensus sequence
```

```
<400> SEQUENCE: 12

Asp Tyr Asp Gly Thr Leu Ser Pro Ile Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Modified B-phosphatase box

<400> SEQUENCE: 13

Asp Tyr Asp Gly Thr Leu Ser Pro Phe Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Consensus sequence

<400> SEQUENCE: 14

Cys Val Ser Val His Phe Arg Cys Val
1               5

<210> SEQ ID NO 15
<211> LENGTH: 9
<212> TYPE: PRT
<213> ORGANISM: Artificial Sequence
<220> FEATURE:
<223> OTHER INFORMATION: Modified consensus sequence

<400> SEQUENCE: 15

Cys Val Ser Val Asp Phe Arg Cys Val
1               5
```

POLYNUCLEOTIDES ENCODING TREHALOSE-6-PHOSPHATE PHOSPHATASE AND METHODS OF USE THEREOF

FIELD OF THE INVENTION

The present invention relates generally to the field of molecular biology and regards various polynucleotides, polypeptides and methods of use that may be employed to enhance yield in transgenic plants. Transgenic plants comprising any one of the polynucleotides or polypeptides described herein may exhibit any one of the traits consisting of increased yield, increased tolerance to abiotic stress, increased cell growth, increased water use efficiency and increased nutrient use efficiency.

STATEMENT REGARDING ELECTRONIC SUBMISSION OF A SEQUENCE LISTING

A Sequence Listing in ASCII text format, submitted under 37 C.F.R. §1.821, entitled 7240 US NP 15 May 2013 CORRECTEDSequenceList ST25. txt, 25.4 KB in size, generated on May 15, 2013 and filed via EFS-Web is provided in lieu of a paper copy. This Sequence Listing is hereby incorporated by reference into the specification for its disclosure.

BACKGROUND OF THE INVENTION

The increasing world population and the dwindling supply of arable land available for agriculture fuels the need for research in the area of increasing the efficiency of agriculture. Conventional means for crop and horticultural improvements utilize selective breeding techniques to identify plants having desirable characteristics. However, such selective breeding techniques have several drawbacks, namely that these techniques are often labor intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant's genome. Such technology has the capacity to deliver crops or plants having various improved economic, agronomic or horticultural traits.

SUMMARY OF THE INVENTION

The following Summary lists several embodiments of the invention subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the invention, whether listed in this Summary or not. To avoid excessive repetition, this Summary does not list or suggest all possible combinations of such features.

The invention provides nucleotide sequences that when transgenically expressed in a plant increases yield and/or increased tolerance to stress. The Trehalose-6-Phosphate Phosphatase (T6PP) proteins described herein comprise modifications or improvements which are associated with increased yield and/or increased tolerance to stress when transgenically expressed in a plant.

The methods disclosed herein further describe the transformation of plants with the polynucleotides encoding modified T6PPs. Transgenic plants comprising the polynucleotides disclosed herein may display increased cell growth, increased plant and/or seedling vigor, increased yield, increased seed weight, increased water use efficiency and increased biomass. Plants produced by the methods herein are contemplated to have an increased tolerance to abiotic stress. It is envisioned that transgenic plants of the invention will confer increased root growth which may have many positive implications in water use and nutrient use efficiency of the plant as well as decreasing the incidence of soil erosion of commercial agricultural land. The transgenic plants described herein will produce higher grain yield in the plant. The transgenic plants herein may confer an increase in yield in both optimal and/or non-optimal growing conditions.

In addition, an embodiment of the invention includes a kit for detecting the nucleic acids unique to a modified T6PP, biological samples derived from a plant, tissue or seed comprising a modified T6PP, and an extract derived from the biological sample. Another embodiment includes antibodies against modified T6PP polypeptides as well as, kits for detecting modified T6PP polypeptides and methods of detecting modified T6PP polypeptides.

These and other features, objects and advantages of the present invention will become better understood from the description that follows. In the description, reference is made to the accompanying sequences, which form a part hereof and in which there is shown by way of illustration, not limitation, embodiments of the invention. The description of preferred embodiments is not intended to limit the invention to cover all modifications, equivalents and alternatives.

BRIEF DESCRIPTION OF THE SEQUENCES IN THE SEQUENCE LISTING nt=nucleotide sequence
pt=protein sequence
SEQ ID NO: 1 Trehalose-6-Phosphate Phosphatase (nt)
SEQ ID NO: 2 Trehalose-6-Phosphate Phosphatase (pt)
SEQ ID NO: 3 Trehalose-6-Phosphate Phosphatase—single modification (nt)
SEQ ID NO: 4 Trehalose-6-Phosphate Phosphatase—single modification (pt)
SEQ ID NO: 5 Trehalose-6-Phosphate Phosphatase—double modification a (nt)
SEQ ID NO: 6 Trehalose-6-Phosphate Phosphatase—double modification a (pt)
SEQ ID NO: 7 Trehalose-6-Phosphate Phosphatase Consensus Sequence
SEQ ID NO: 8 Trehalose-6-Phosphate Phosphatase PPase domain
SEQ ID NO: 9 Trehalose-6-Phosphate Phosphatase A-Phosphatase box
SEQ ID NO: 10 Trehalose-6-Phosphate Phosphatase B-Phosphatase box
SEQ ID NO: 11 OsMADS6 Promoter
SEQ ID NO: 12 B-Phosphatase box consensus
SEQ ID NO: 13 Modified B-Phosphatase box consensus
SEQ ID NO: 14 Consensus sequence
SEQ ID NO: 15 Modified consensus sequence

DETAILED DESCRIPTION OF THE INVENTION

The practice of the present invention will employ, unless otherwise indicated, conventional techniques of botany, microbiology, tissue culture, molecular biology, chemistry, biochemistry, plant quantitative genetics, statistics and recombinant DNA technology, which are within the skill of the art. Such techniques are explained fully in the literature. See, e.g., Langenheim and Thimann, (1982) Botany: Plant Biology and Its Relation to Human Affairs, John Wiley; Cell Culture and Somatic Cell Genetics of Plants, vol. 1, Vasil, ed. (1984); Stanier, et al., (1986) The Microbial World, 5th ed., Prentice-Hall; Dhringra and Sinclair, (1985) Basic Plant Pathology Methods, CRC Press; Maniatis, et al., (1982) Molecular Cloning: A Laboratory Manual; DNA Cloning, vols. I and II, Glover, ed. (1985); Oligonucleotide Synthesis, Gait, ed. (1984); Nucleic Acid Hybridization, Hames and Higgins, eds. (1984); and the series Methods in Enzymology, Colowick and Kaplan, eds, Academic Press, Inc., San Diego, Calif.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

Unless otherwise defined, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention.

As used herein the singular forms "a", "and", and "the" include plural reference unless the context clearly dictates otherwise. Thus, for example, reference to "a vector" is a reference to one or more vectors and includes equivalents thereof known to those skilled in the art.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent.

As used herein, the word "or" means any one member of a particular list and also includes any combination of members on that list.

The terms "comprises", "comprising", "includes", "including", "having" and their conjugates mean "including but not limited to". The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals there between. As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), O-Beta Replicase systems, transcription-based amplification system (TAS) and strand displacement amplification (SDA). See, e.g., Diagnostic Molecular Microbiology: Principles and Applications, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is Micrococcus rubens, for which GTG is the methionine codon (Ishizuka, et al., (1993) J. Gen. Microbiol. 139:425-32) can be modified to yield a functionally identical molecule. Accordingly, each silent variation of a nucleic acid, which encodes a polypeptide of the present invention, is implicit in each described polypeptide sequence and incorporated herein by reference.

A "control plant" or "control" as used herein may be a non-transgenic plant of the parental line used to generate a transgenic plant herein. A control plant may in some cases be a transgenic plant line that includes an empty vector or marker gene, but does not contain the recombinant polynucleotide of the present invention that is expressed in the transgenic plant being evaluated. A control plant in other cases is a transgenic plant expressing the gene with a constitutive promoter. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V) and
6) Phenylalanine (F), Tyrosine (Y), Tryptophan (W). See also, Creighton, Proteins, W.H. Freeman and Co. (1984).

As used herein the terms "modified" or "modification" interchangeably refer to deliberate or random substitutions, deletions or additions to a nucleic acid, peptide, polypeptide or protein sequence which alters, adds or deletes at least one amino acid residue within a given polypeptide. A "modified T6PP" as used herein refers to any nucleic acid encoding a T6PP or peptides, polypeptides or protein having T6PP activity either of which having been modified so that the resultant T6PP confers modified T6PP activity and/or modified binding to T6P resulting in improved yield and/or abiotic stress tolerance in a plant when compared to an unmodified T6PP.

As used herein "homologous position" refers to the position of one or more amino acids in a polypeptide or one or more base pairs in a polynucleotide sequence that are in a similar or equivalent position in a second polypeptide or polynucleotide that is an ortholog, paralog or homolog to the original polypeptide or polynucleotide. The position of the amino acids may be in the same functional region of the two proteins but may not be at the exact numeric position of the amino acid between the two polypeptide sequences. The homologous position of amino acids on two proteins can be determined by several methods well known in the art including, for example, sequence alignment (e.g. BLAST), three dimensional protein modeling (see for example, Sander C. and Scheider R., (1991) PROTEINS: Structure, Function and Genetics 9:56-68) and the like.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium Mycoplasma capricolum (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the invention, which contains a vector and supports the replication and/or expression of the expression vector. Host cells may be prokaryotic cells such as E. coli, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., nucleus, chromosome, plasmid, plastid or mitochondrial DNA), converted into an autonomous replicon or transiently expressed (e.g., transfected mRNA).

As used herein "gene stack" refers to the introduction of two or more genes into the genome of an organism. In certain aspects of the invention it may be desirable to stack any abiotic stress gene (e.g. cold shock proteins, genes associated with ABA response) with the T6PPs as described herein. Likewise, it may also be desirable to stack the T6PPs as described herein with genes conferring insect resistance, disease resistance, increased yield or any other beneficial trait (e.g. increased plant height, etc) known in the art.

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "T6PP nucleic acid" means a nucleic acid comprising a polynucleotide ("T6PP polynucleotide") encoding a full length or partial length "T6PP polypeptide".

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise in one case a substantial representation of the entire transcribed fraction of a genome of a specified organism. Construction of exemplary nucleic acid libraries, such as genomic and cDNA libraries, is taught in standard molecular biology references such as Berger and Kimmel, (1987) Guide To Molecular Cloning Techniques, from the series Methods in Enzymology, vol. 152, Academic Press, Inc., San Diego, Calif.; Sambrook, et al., (1989) Molecular Cloning: A Laboratory Manual, 2nd ed., vols. 1-3; and Current Protocols in Molecular Biology, Ausubel, et al., eds, Current Protocols, a joint venture between Greene Publishing Associates, Inc. and John Wiley & Sons, Inc. (1994 Supplement). In another instance "nucleic acid library" as defined herein may also be understood to represent libraries comprising a prescribed faction or rather not substantially representing an entire genome of a specified organism. For example, small RNAs, mRNAs and methylated DNA. A nucleic acid library as defined herein might also encompass variants of a particular molecule (e.g. a collection of variants for a particular protein).

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particular plant is *Zea mays*.

As used herein, "yield" may include reference to bushels per acre of a grain crop at harvest, as adjusted for grain moisture (15% typically for maize, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art. In certain embodiments of the invention yield may be increased in stressed and/or non-stressed conditions.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such as *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions in most cells.

Any suitable promoter sequence can be used by the nucleic acid construct of the present invention. According to some embodiments of the invention, the promoter is a constitutive promoter, a tissue-specific, or an abiotic stress-inducible promoter.

Suitable constitutive promoters include, for example, CaMV 35S promoter (SEQ ID NO:1546; Odell et al., Nature 313:810-812, 1985); *Arabidopsis* At6669 promoter (SEQ ID NO:1652; see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1);107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608, 144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143).323-32 1990), napA (Stalberg, et al., Planta 199: 515-519, 1996), Wheat SPA (Albanietal, Plant Cell, 9: 171-184, 1997), sunflower oleosin (Cummins, etal., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice -globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters [e.g., rice OSH1 (Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, plant reproductive tissues [e.g., OsMADS promoters (U.S. Patent Application 2007/0006344)].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The term "Enzymatic activity" is meant to include demethylation, hydroxylation, epoxidation, N-oxidation, sulfooxidation, N-, S-, and O-dealkylations, desulfation, deamination, and reduction of azo, nitro, and N-oxide groups. The term "nucleic acid" refers to a deoxyribonucleotide or ribonucleotide polymer in either single- or double-stranded form, or sense or anti-sense, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "structural gene" is that portion of a gene comprising a DNA segment encoding a protein, polypeptide or a portion thereof, and excluding the 5' sequence which drives the initiation of transcription. The structural gene may alternatively encode a nontranslatable product. The structural gene may be one which is normally found in the cell or one which is not normally found in the cell or cellular location wherein it is introduced, in which case it is termed a "heterologous gene". A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications that could affect biological activity or its characteristics, the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bounded by the appropriate splice junctions. The structural gene may be translatable or non-translatable, including in an anti-sense orientation. The structural gene may be a composite of segments derived from a plurality of sources and from a plurality of gene sequences (naturally occurring or synthetic, where synthetic refers to DNA that is chemically synthesized).

"Derived from" is used to mean taken, obtained, received, traced, replicated or descended from a source (chemical and/or biological). A derivative may be produced by chemical or biological manipulation (including, but not limited to, substitution, addition, insertion, deletion, extraction, isolation, mutation and replication) of the original source.

"Chemically synthesized", as related to a sequence of DNA, means that portions of the component nucleotides were assembled in vitro. Manual chemical synthesis of DNA may be accomplished using well established procedures (Caruthers, Methodology of DNA and RNA Sequencing, (1983), Weissman (ed.), Praeger Publishers, New York, Chapter 1); automated chemical synthesis can be performed using one of a number of commercially available machines.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, an "expression cassette" is a nucleic acid construct, generated recombinantly or synthetically, with a series of specified nucleic acid elements, which permit transcription of a particular nucleic acid in a target cell. The expression cassette can be incorporated into a plasmid, chromosome, mitochondrial DNA, plastid DNA, virus or nucleic acid fragment. Typically, the expression cassette portion of an expression vector includes, among other sequences, a nucleic acid to be transcribed and a promoter.

The terms "residue" or "amino acid residue" or "amino acid" are used interchangeably herein to refer to an amino acid that is incorporated into a protein, polypeptide or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m = 81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5xDenhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

"Overexpression" refers to the level of expression in transgenic organisms that exceeds levels of expression in normal or untransformed organisms.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Preferred expression", "Preferential transcription" or "preferred transcription" interchangeably refers to the expression of gene products that are preferably expressed at a higher level in one or a few plant tissues (spatial limitation) and/or to one or a few plant developmental stages (temporal limitation) while in other tissues/developmental stages there is a relatively low level of expression.

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

A "selectable marker gene" refers to a gene whose expression in a plant cell gives the cell a selective advantage. The selective advantage possessed by the cells transformed with the selectable marker gene may be due to their ability to grow in presence of a negative selective agent, such as an antibiotic or a herbicide, compared to the ability to grow of non-transformed cells. The selective advantage possessed by the transformed cells may also be due to their enhanced capacity, relative to non-transformed cells, to utilize an added compound as a nutrient, growth factor or energy source. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

The term "transformation" refers to the transfer of a nucleic acid fragment into the genome of a host cell, resulting in genetically stable inheritance. "Transiently transformed" refers to cells in which transgenes and foreign DNA have been introduced (for example, by such methods as *Agrobacterium*-mediated transformation or biolistic bombardment), but not selected for stable maintenance. "Stably transformed" refers to cells that have been selected and regenerated on a selection media following transformation.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "translational enhancer sequence" refers to that DNA sequence portion of a gene between the promoter and coding sequence that is transcribed into RNA and is present in the fully processed mRNA upstream (5') of the translation start codon. The translational enhancer sequence may affect processing of the primary transcript to mRNA, mRNA stability or translation efficiency. "Visible marker" refers to a gene whose expression does not confer an advantage to a transformed cell but can be made detectable or visible. Examples of visible markers include but are not limited to P-glucuronidase (GUS), luciferase (LUC) and green fluorescent protein (GFP).

"Wild-type" refers to the normal gene, virus, or organism found in nature without any mutation or modification.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

As used herein "Protein extract" refers to partial or total protein extracted from a plant part. Plant protein extraction methods are well known in the art.

As used herein "Plant sample" refers to either intact or non-intact (e g milled seed or plant tissue, chopped plant tissue, lyophilized tissue) plant tissue. It may also be an extract comprising intact or non-intact seed or plant tissue.

The following terms are used to describe the sequence relationships between two or more nucleic acids or polynucleotides or polypeptides: (a) "reference sequence," (b)

"comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, and 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.*, 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40 and 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988)

*Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The phrase "abiotic stress" as used herein refers to any adverse effect on metabolism, growth, reproduction and/or viability of a plant by abiotic factors (i.e. water availability, heat, cold, and etc). Accordingly, abiotic stress can be induced by suboptimal environmental growth conditions such as, for example, salinity, water deprivation, water deficit, drought, flooding, freezing, low or high temperature (e g , chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress without suffering a substantial alteration in metabolism, growth, productivity and/or viability.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water to support the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can reduce yield, stunt growth or retard development. Plants can recover from some periods of water deficit stress without significantly affecting yield. However, water deficit at the time of pollination can lower or reduce yield. Thus, a useful period in the life cycle of corn, for example, for observing response or tolerance to water deficit is the late vegetative stage of growth before tassel emergence or the transition to reproductive development. Tolerance to water deficit is determined by comparison to control plants. For instance, plants of this invention can produce a higher yield than control plants when exposed to water deficit. In the laboratory and in field trials drought can be simulated by giving plants of this invention and control plants less water than is given to sufficiently-watered control plants and measuring differences in traits. One aspect of the invention provides plants overexpressing the genes as disclosed herein which confers a higher tolerance to a water deficit.

As used herein, the phrase "water optimization" refers to any measure of a plant, its parts, or its structure that can be measured and/or quantified in order to assess an extent of or a rate of plant growth and development under different conditions of water availability. As such, a "water optimization trait" is any trait that can be shown to influence yield in a plant under different sets of growth conditions related to water availability. Exemplary measures of water optimization are grain yield at standard moisture percentage (YGSMN), grain moisture at harvest (GMSTP), grain weight per plot (GWTPN), and percent yield recovery (PYREC).

As used herein, the phrases "drought tolerance" and "drought tolerant" refer to a plant's ability to endure and/or thrive under conditions where water availability is suboptimal. In general, a plant is labeled as "drought tolerant" if it displays "enhanced drought tolerance." As used herein, the phrase "enhanced drought tolerance" refers to a measurable improvement, enhancement, or increase in one or more water optimization phenotypes as compared to one or more control plants.

Water Use Efficiency (WUE) is a parameter frequently used to estimate the tradeoff between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $^{13}C/^{12}C$ fixed in plant tissue, and measured with an isotope ratio mass-spectrometer, also has been used to estimate WUE in plants using C-3 photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is contemplated that the transgenic plants produced by the methods described herein will confer an increase in water use efficiency.

The phrase "biotic stress" as used herein refers to any adverse effect on metabolism, growth, reproduction and/or viability of a plant by biotic factors (i.e. insect pressure, disease and etc).

The phrase "biotic stress tolerance" as used herein refers to the ability of a plant to endure a biotic stress without suffering a substantial alteration in metabolism, growth, reproduction and/or viability.

As used herein the phrase "plant biomass" refers to the amount (measured in grams of air-dry or dry tissue) of a tissue produced from the plant in a growing season, which could also determine or affect the plant yield or the yield per growing area.

As used herein the phrase "plant vigor" refers to the amount (measured by weight) of tissue produced by the plant in a given time. Hence increased vigor could determine or affect the plant yield or the yield per growing time or growing area.

The term "early vigor" refers to active healthy well-balanced growth especially during early stages of plant growth, and may result from increased plant fitness due to, for example, the plants being better adapted to their environment (optimizing the use of energy resources and partitioning between shoot and root). Plants having early vigor also show increased seedling survival and a better establishment of the crop, which often results in highly uniform fields (e.g. crops growing in a uniform fashion, such as the crops reaching various stages of development at substantially the same time), and often higher yields. Therefore, early vigor may be determined by measuring various factors, such as thousand kernel weight, percentage germination, percentage emergence, seedling growth, seedling height, root length, root and shoot biomass and many more.

As used herein, "seedling vigor" refers to the plant characteristic whereby the plant emerges from soil faster, has an increased germination rate (i.e., germinates faster), has faster and larger seedling growth and/or germinates faster under cold conditions as compared to the wild type or control under similar conditions. Seedling vigor has often been defined to comprise the seed properties that determine "the potential for rapid, uniform emergence and development of normal seedlings under a wide range of field conditions".

The life cycle of flowering plants in general can be divided into three growth phases: vegetative, inflorescence, and floral (late inflorescence phase). In the vegetative phase, the shoot apical meristem (SAM) generates leaves that later will ensure the resources necessary to produce fertile offspring. Upon receiving the appropriate environmental and developmental signals the plant switches to floral, or reproductive, growth and the SAM enters the inflorescence phase (I) and gives rise to an inflorescence with flower primordia. During this phase the fate of the SAM and the secondary shoots that arise in the axils of the leaves is determined by a set of meristem identity genes, some of which prevent and some of which promote the development of floral meristems. Once established, the plant enters the late inflorescence phase where the floral organs are produced. If the appropriate environmental and developmental signals are present the plant switches to floral, or reproductive, growth. If such signals are disrupted, the plant will not be able to enter reproductive growth, therefore maintaining vegetative growth.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

Antibodies of the invention include polyclonal and monoclonal antibodies and mixtures thereof, which can be any of IgG, IgA, IgM, IgE, IgD, and any isotype thereof, for example, IgG1, IgG2, IgG3 or IgG4. In the case of a monoclonal antibody, an exemplary class of antibody is IgG. Subclasses of IgG include, for example, IgG1, IgG2, IgG3 and IgG4. Antibodies include intact and chimeric immunoglobulin molecules with two full-length heavy chains and two full-length light chains (e.g., mature portion of heavy and light chain variable region sequences) as well as subsequences/fragments of heavy or light chain which retain at least a part of a function (e.g. T6PP binding specificity or T6PP binding affinity) of parental intact antibody that specifically binds T6PP and in particular a modified T6PP. Subsequences can have the same or substantially the same binding specificity, binding affinity as parental intact and chimeric antibodys.

Monoclonal or polyclonal antibody production may be effected by techniques which are well known in the art. "Polyclonal" antibodies are antibodies obtained from different B cells resources. They are a combination of immunoglobulin molecules that secret a specific antigen, each identifying a different epitope. Polyclonal antibodies are typically produced by inoculation into a suitable mammal, such as a mouse, rabbit or goat. For example, a composition containing a T6PP protein capable of producing an antigen is injected into the mammal. The presence of the new protein induces the B-lymphocytes to produce IgG immunoglobulins specific for the T6PP antigen. The polyclonal IgG immunoglobulins are then purified from the mammal's serum.

The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with a T6PP of the present invention. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986).

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Plants engineered for improved yield under various biotic and abiotic stresses is of special interest in the field of agriculture. For example, abiotic stress is a primary cause of crop loss worldwide, reducing average yields for most major crop plants by more than 50% (Wang et al., Planta (2003) 218: 1-14). Abiotic stresses may be caused by drought, floods, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

In some instances plant yield is relative to the amount of plant biomass a particular plant may produce. A larger plant with a greater leaf area can typically absorb more light, nutrients and carbon dioxide than a smaller plant and therefore will likely gain a greater weight during the same period (Fasoula & Tollenaar 2005 Maydica 50:39). Increased plant biomass may also be highly desirable in processes such as the conversion of biomass (e.g. corn, grasses, sorghum, cane) to fuels such as for example ethanol or butanol.

The ability to increase plant yield would have many applications in areas such as agriculture, the production of ornamental plants, arboriculture, horticulture, biofuel production, pharmaceuticals, enzyme industries which use plants as factories for these molecules and forestry. Increasing yield may also find use in the production of microbes or algae for use in bioreactors (for the biotechnological production of substances such as pharmaceuticals, antibodies, vaccines, fuel or for the bioconversion of organic waste) and other such areas.

Plant breeders are often interested in improving specific aspects of yield depending on the crop or plant in question, and the part of that plant or crop which is of relative economic value. For example, a plant breeder may look specifically for improvements in plant biomass (weight) of one or more parts of a plant, which may include aboveground (harvestable) parts and/or harvestable parts below ground. This is particularly relevant where the aboveground parts or below ground parts of a plant are for consumption. For many crops, particularly cereals, an improvement in seed yield is highly desirable. Increased seed yield may manifest itself in many ways with each individual aspect of seed yield being of varying importance to a plant breeder depending on the crop or plant in question and its end use.

It would be of great advantage to a plant breeder to be able to pick and choose the aspects of yield to be altered. It may also be highly desirable to be able to pick a gene suitable for altering a particular aspect of yield (e.g. seed yield, biomass weight, water use efficiency, yield under stress conditions). For example an increase in the fill rate, combined with increased thousand kernel weight would be highly desirable for a crop such as corn. For rice and wheat a combination of increased fill rate, harvest index and increased thousand kernel weight would be highly desirable.

It has now been discovered that the expression of several forms of trehalose-6-phosphate phosphatase (T6PP) in plants confers a significant increase in yield as well as confer resistance to various types of stress (i.e. abiotic stress). During the course of analyzing various T6PP variants transgenically expressed in plants it has been found that the transgenic plants showing the highest yield in seed also comprised T6PPs with modifications to amino acid residues associated with substrate binding. Not to be limited by theory, these proteins may have decreased enzymatic activity when directly compared to a T6PP not containing these modifications. Further, not to be limited by theory, it appears that expressing a T6PP in plant with decreased enzymatic activity results in a beneficial phenotype having significant increased yield in both stress (e.g. drought) and non-stressed field conditions. Again, not to be limited by theory, this may suggest that a less active form of T6PP serves as a molecular signal therefore conferring in the plant an increase in starch, sugar and increased seed yield. In theory, this molecular signal could be a protein-protein interaction with trehalose-6-phosphate synthase (T6PS) forming a complex that then may provide a signal to the plant. In theory this signal may be altered levels of trehalose-6-phosphate (T6P). Not to be limited by theory, but one possibility is that a modified T6PP when expressed in a plant forms a protein-protein complex with endogenous forms of T6PS and/or T6PP. In theory, this binding alters T6PP's ability to hydrolyze its substrate T6P and activates or modulates T6PS to produce T6P. This interaction then confers altered levels of T6P that then signal to the plant to commit more sugars to seed and/or biomass. Alternatively, not to be limited by theory, the modified T6PP having decreased activity interacts with some other component not yet identified which results in the initiation of a cascade to signal to the plant to commit more sugars to yield and/or biomass. Based upon the theories above, many methods may be employed to produce a plant with increased yield under any condition. It is also envisioned that one could use the methods described herein to modulate the production of sugars in a plant and further employ molecular engineering techniques to transport sugars to various parts of the plants to increase for instance such things as plant biomass, seed yield, sugar content in aboveground plant material (i.e. such as sugarcane), and to consumable plant parts. Additionally these trehalose-6-phosphate phosphatase genes may find use in conferring many more desirable traits such as early vigor, stress tolerance, drought tolerance, increased nutrient use efficiency, increased root mass and increased water use efficiency.

T6PP is an enzyme involved in the trehalose biosynthesis pathway. Trehalose, a non-reducing disaccharide consisting of two glucose molecules linked via alpha-1,1 bonds. The sugar trehalose can be found in many various organisms across multiple kingdoms (e.g. plants, bacteria, insects, etc). Trehalose has been shown to be involved in carbohydrate storage function and has been further associated to play a role in stress tolerance in bacteria, fungi and insects. In plants, trehalose was initially thought to be confined to extremophiles such as the resurrection plant *Selaginella lepidophylla*, however it is now widely accepted that trehalose metabolism is ubiquitous in the plant kingdom.

Trehalose is synthesized from UDP-glucose and Glucose-6-phosphate in two enzymatic reactions. First UDP-glucose and Glucose-6-phosphate are converted to UDP (uridine diphosphate) and alpha, alpha-trehalose 6-phosphate (T6P) by the enzyme T6PS (trehalose phosphate synthase). In a second step, which is catalyzed by the enzyme T6PP (trehalose phosphate phosphatase), T6P is de-phosphorylated to produce trehalose and orthophosphate.

In yeast, the two enzymatic activities (T6PS and T6PP activity) reside in a large protein complex, containing the active subunits, T6PS 1 and T6PS2, and the regulatory subunits, with T6PS1 having T6PS activity and T6PS2 having T6PP activity. In E. coli, the two enzymatic activities are found in separate protein complexes. In plants, the protein complex has not been characterized to date.

In *Arabidopsis thaliana*, trehalose biosynthetic enzymes have been classified into three classes:

Class I: containing four genes, AtT6PS1 to AtT6PS4 having high similarity to ScT6PS1;

Class II: having seven members, AtT6PS5 to AtT6PS1 1, with high sequence similarity to ScT6PS2; and Class III:, containing 10 members, AtT6PPA to AtT6PPJ, encoding proteins with similarity to E. coli T6PS2 and the C-terminus of ScT6PS2 proteins.

Genes encoding proteins within these classes are also present in other plant species.

Within Class I and Class II, enzymatic activity has only been unambiguously determined for AtT6PS1, which displays T6PS activity (Blazquez et al. Plant J. March 1998;13 (5):685-9.). Surprisingly, no T6PP activity has been reported to date for any of the other Class II T6PS proteins. In contrast, T6PP activity was previously described for AtT6PPA and AtT6PPB, two of the members of Class III (Vogel et al. Plant J. March 1998;13(5):673-83). Plant Class III T6PPs contain two phosphatase consensus sequence motifs found in all T6PP enzymes described to date (Thaller et al. Protein Sci. July 1998;7(7):1647-52).

The genetic manipulation of trehalose biosynthesis genes has been reported to lead to improved stress tolerance in plants, as well as causing striking developmental alterations. Overexpression of E. coli OtsA and OtsB genes (equivalents to T6PP and T6PS) in transgenic tobacco and potato plants was reported to cause developmental aberrations in roots and leaves as well as stunted plant growth. Fewer seeds were produced in the OtsA transgenic tobacco plants and the OtsB transgenic potato plants did not produced tubers (Goddijn et al. Plant Physiol. January 1997;113(1):181-90). Similar results have been described by others (Holmstrom et al. Nature, 379, 683-684; Romero et al. Planta, 201, 293-297; Pilont-Smits et al. 1998; J Plant Physiol. 152:525-532; Schluepmann et al. Proc Natl. Acad. Sci. U S A. 2003;100 (11):6849-54). Mutants defective in T6PS and T6PP genes have also reportedly shown developmental defects. T6PS 1 knock out mutants in Arabidopsis showed impaired embryo development (Eastmond et al. Plant J. January 2002; 29(2): 225-35). McSteen et. al. (Plant Cell 2006; 18; 518-522) mentions the isolation and characterization of a maize geneRAMOSA3 (RA3) reported to be responsible for meristem development and inflorescence development including branching. It is suggested that the gene, gene product, and regulatory regions may be used to manipulate branching, meristem growth, inflorescence development and arrangement. Negative phenotypes associated with the expression of a transgene can have detrimental effects to a plant's relative yield. For example, without seed set, seed filling, fertility of a plant etc. there would be no increase in seed yield. Patent application U.S. 2007/0006344 describes the expression of a T6PP in a plant to confer an increase in plant yield without any negative phenotypes and/or detrimental effects to the plant biological function and is hereby incorporated by reference. U.S. Patent Application 2007/0006344 describes the use of a trehalose-6-phosphate phosphatase operably linked to a maternal reproductive tissue preferred promoter (e.g. OsMADS 6 promoter) that targets the preferential expression of the T6PP to maternal reproductive tissue of a plant which resulted in a significant yield increase in maize under stress and non-stress conditions. The following invention generally involves the identification of T6PP having modifications that confer improved yield and field efficacy in crop plants and further describes methods one may use to increase yield in a plant by utilizing modified T6PPs in a plant.

The invention provides nucleotide sequences that when transgenically expressed in a plant increases plant vigor, yield and/or biomass under stress or non-stress conditions. It was discovered that the T6PP proteins comprising modifications which alter the activity of the T6PP protein wherein the activity is decreased when directly compared to a relative T6PP not having the modifications, confer a significant increase in both yield and/or increased tolerance to stress when these modified T6PPs are transgenically expressed in a plant. Not to be limited by theory, these modifications appear to be made at key positions within the T6PP protein which influence the binding of T6PP to its substrate T6P or allow advantageous alterations in the overall confirmation of the T6PP, which alters protein-protein interactions. In theory, the T6PPs as disclosed herein having decreased activity serves as a signal to the plant or initiates in the plant certain metabolic cascades or metabolic pathways which confer in the plant increased sugar transport to the fruit, grain, leaves, roots or other parts thus resulting in increased seed yield, biomass and/or root growth. In another embodiment, not to be limited by theory, a T6PP modified to have decreased activity and/or decreased binding to T6P and/or increased binding to T6PS forms a protein complex with endogenous T6PS when said modified T6PP is transgenically expressed in a plant herein referred to a "T6PP/T6PS complex" or "complex". The complex may contain additional proteins in combination with T6PP and T6PS. Not to be limited by theory, expression of a T6PP modified for decreased activity and/or modified to have increased binding potential to an endogenous T6PS protein or other protein(s) within the complex may be used to create an improved complex which confers in the plant increased yield and/or increased tolerance to stress. In another embodiment, not to be limited by theory, the complex confers in the plant modified levels of T6P which then confer in the plant increased yield and/or increased tolerance to stress. In one aspect of the invention a transgenic T6PP/TSPS complex may be transgenically expressed in a plant to confer increased yield and/or increased stress tolerance in a plant. In another embodiment, it is contemplated that various chemical structures and or molecular structures may be constructed via methods well known in the respective art to mimic the function of a T6PP/TSPS complex such as those described herein. In one embodiment, not to be limited by theory, any T6PP may be modified to have decreased substrate binding to T6P which then will confer increased yield and field efficacy when the modified T6PP are expressed transgenically in plants. In some cases the nucleotide sequences encode a protein involved in the trehalose biosynthesis pathway, in one embodiment the protein encodes a T6PP. In another embodiment of the invention, the T6PPs polynucleotides are isolated from the genome of an angiosperm and then modified as described herein. In a further embodiment of the invention the T6PP gene is isolated from a monocot. In one aspect, the T6PP genes, disclosed herein, are isolated from the genome of a rice plant. The T6PP genes described herein are primarily members of the HAD superfamily of phosphatases or comprise a protein consensus sequence as depicted in SEQ ID NO: 7. The HAD phosphatase super family which may also be referred to as the DDDD superfamily of phosphatases comprise a conserved alpha/beta core domain as well as a cap domain whose function may vary (i.e. substrate binding, etc). In one embodiment of the invention, a modification is located in any one of the cap domain, PPase domain, A-Phosphatase box domain or the B-Phosphatase box domain of the T6PP wherein the said modification alters the binding to its substrate (e.g. T6P) and/or expression of T6PP. In another embodiment the modifications may comprise one or more of a substitution, deletion, or addition of one or more amino acid residues to the a relative T6PP protein consensus sequence as depicted in SEQ ID NO: 7 wherein the substitution, deletion or addition of one or more amino acid residues confer altered enzymatic activity of said T6PP and/or modified levels of T6P when the T6PP is transgenically expressed in a plant. Not to be limited by theory, it is believed that creating T6PP protein variants having reduced catalytic activity (i.e. decreased hydrolysis of T6P) creates a signal within the plant conferring increased yield and/or increased tolerance to stress (e.g. drought, heat, cold). In theory, it may be that a T6PP having decreased activity interacts with T6PS forming a protein-protein complex. Again not to be limited in theory, it is believed that the protein-protein interaction forming a T6PP/T6PS complex may activate T6PS thus catalyzing T6P synthesis initiating T6PS to convert Glucose 6-Phosphate and UDP-Glucose to T6P. In one aspect of the invention the T6PP protein variants comprise a modification that decreases the binding of said T6PP to its substrate T6P thus causing a modified level of T6P in the plant. In theory this modified level of T6P then confers in the plant increased yield and/or increased tolerance to stress (abiotic or biotic). In theory, the modified T6PP modified may serve as a metabolic signal to the plant to commit sugars to the production of seed and/or sugars. Additionally these modified T6PPs may also serve as metabolic signals to initiate processes that confer in the plant increased tolerance to abiotic and/or biotic stresses. Again not to be limited by theory, it is believed that the plants expressing modified T6PPs will have a modified level of trehalose as compared to a control plant or as compared to a transgenic plant overexpressing the wild type form of T6PP. Additionally, it is envisioned that plants expressing modified T6PP variants will have a modified level of T6P and/or sugar and a modified level of trehalose. It is also envisioned that any T6PP regardless of activity level may be engineered to form a protein-protein complex with a T6PS thus activating T6PS to modify the production of T6P and modify the rate of T6P hydrolysis wherein the formation of the protein-protein complex and/or the modification in T6P production and/or the presence of a T6PP with altered activity upon formation of the T6PP/T6PS complex confers increased yield and/or increased stress tolerance when said T6PP is expressed in a plant. It is envisioned that any T6PP or enzyme having T6PP activity may be engineered to improve the complex and thus be employed to generate transgenic plants or organisms (e.g. algae) having increased yield. In one embodiment of the invention, proteins comprising a consensus sequence such as depicted in SEQ ID NO: 7 may be employed in the methods as described herein. As used herein the term "reduced activity" refers to any decrease in T6PP activity. For instance an enzyme modified to have 1%, 5%, 10%, 20%, 30%, 40%, 50%, 60%, 65%, 70%, 75%, 80%, 85%, 90%, 95%, 96%, 97%, 98%, 99%, or 100% decrease in T6PP activity relative to a control or native T6PP gene may find use in producing transgenic plants with increased yield. In one embodiment of the invention, the T6PP polypeptide comprises a amino acid sequence having 50%, 60%, 70%, 80%, 90%, 95% or 99% sequence identity to the consensus sequence as described in SEQ ID NO: 7. In a further embodiment the T6PP comprises a consensus sequence as described in SEQ ID NO: 7 wherein at least one modification (inclusive of amino acid substitution, amino acid deletion, amino acid addition) is carried out and said modification reduces activity of said T6PP and/or increases the likelihood of said T6PP to form a protein-protein complex with T6PS. In another embodiment plants expressing a T6PP variant having decreased activity and/or a T6PP having an increased likelihood of forming a protein-protein complex with T6PS will have a modified level of T6P as compared to a control not expressing a modified T6PP wherein the modified level of T6P confers in the plant increased yield (e.g. seed yield, biomass, vigor), cell growth, sugar content, starch content and increased tolerance to stress (drought, heat, cold, salinity, flood, abiotic, and/or biotic stress). In another embodiment of the invention, expression of a modified T6PP in a plant is directed to plant reproductive tissue. In another embodiment of the invention patterns of gene expression might be important in expanding duration of drought tolerance in a plant. For instance, one may construct expression cassettes to express a modified T6PP during plant flowering thus conferring drought tolerance for this stage of development of the plant. Likewise, one may also construct expression cassettes that constitutively expresses a modified T6PP in a plant thus, not to be limited by theory, confers drought tolerance throughout the plant's lifecycle. It is contemplated that T6PPs may be modeled to have altered activity via modifications outside the conserved amino acid residues of the consensus sequence as depicted in SEQ ID NO: 7 wherein the modification alters the binding of T6PP to T6P and/or said modifications increasing the likelihood that the T6PP will form a protein-protein interaction with one or proteins within the complex. In one embodiment one may decrease the activity of T6PP by irradiation of DNA and thus producing variants having decreased activity when expressed in a plant. Likewise it is contemplated that one may use common techniques such as gene shuffling to produce variants of T6PP having decreased activity. Not to be limited by theory, it is envisioned that one may create chemical orthogonal structures that may in a sense mimic an inactive T6PP protein structure and in one embodiment form a complex with a plant T6PS therefore conferring in a plant increased yield. In another embodiment, one may create a chemical orthogonal structure that may mimic the structure of a T6PP/T6PS complex which then can be applied to plants (e.g. chemical application) to confer increased yield and stress tolerance (i.e. drought tolerance). It is envisioned that chemical orthogonal structures may be applied to a plant to modulate sugar transport at given reproductive or developmental stages of the plant. It is contemplated that the T6PP genes from any class or family may be employed in any of the methods and/or aspects of the invention disclosed herein. It is further contemplated that T6PP genes with similar sequence homology (e.g. greater than or equal to 50% 75%, 80% or 85% sequence identity to SEQ ID NO: 1, 3, or 5 and/or molecular structure isolated or synthesized may be employed in the embodiments as described herein. T6PP has been shown to be ubiquitous amongst members of the plant kingdom and many instances have been shown to have conserved function across multiple genus and species of plants. Therefore, it is contemplated that a synthetic nucleic acid encoding a T6PP protein conferring decreased activity and/or modified binding to T6P and/or modified binding to T6PS could be employed in the methods disclosed herein to confer plants with favorable traits (e.g. increased yield, increased biomass, increased plant vigor) as described herein.

The methods disclosed herein further describe the transformation of plants with the polynucleotides such as disclosed herein. Transgenic plants comprising the polynucleotides disclosed herein may display increased cell growth, increased plant and/or seedling vigor, increased yield, increased seed weight and increased biomass. Plants produced by the methods herein are contemplated to have an increased tolerance to both biotic and abiotic stress. It is envisioned that transgenic plants of the invention will confer increased root growth which may have many positive implications in water use and nutrient use efficiency of the plant as well as decreasing the incidence of soil erosion of commercial agricultural land. It is also contemplated that the plants comprising the polynucleotides as described herein may also display higher tolerance to insect feeding due to increased growth. In some instances, the plants described in the invention will have increased standability and/or reduced risk of crop lodging, therefore conferring transgenic plants that can withstand weather conditions such as strong winds or hail. The transgenic plants described herein may produce higher yield in both biomass yield and grain yield of the plant. One aspect of the invention provides various modifications one may perform on a given T6PP gene sequence that may be employed in transgenic plants to confer increased yield. The transgenic plants herein may confer a increase in yield in both optimal and/or non-optimal growing conditions.

Any reference hereinafter to a "protein useful in the methods of the invention" is taken to mean a T6PP polypeptide as defined herein. Any reference hereinafter to a "nucleic acid useful in the methods of the invention" is taken to mean a nucleic acid capable of encoding such a T6PP polypeptide.

A preferred method for modulating expression of a nucleic acid encoding a T6PP protein useful in the methods of the invention is by introducing and expressing in a plant a nucleic acid encoding a protein useful in the methods of the invention as defined below.

The nucleic acid to be introduced into a plant (and therefore useful in performing the methods of the invention) is any nucleic acid encoding a T6PP. A "T6PP polypeptide" as defined herein refers to any polypeptide with trehalose-6-phosphate phosphatase activity comprising at least one trehalose-phosphate-phosphatase (Trehalose-PPase) domain. Trehalose-PPase domains are typically between 200 and 250 amino acids in length and typically comprise a phosphatase consensus sequence motif that is found in all T6PP enzymes described to date (Thaller et al. 1998). The amino acid sequence for the Trehalose-PPase domain is given in SEQ ID NO: 8. A person skilled in the art will readily be able to identify the presence of a Trehalose-PPase domain using tools and techniques known in the art. This phosphatase consensus sequence motif typically comprises two phosphatase boxes, named A and B-Phosphatase Box. SEQ ID NO: 9 represents a consensus sequence for Phosphatase box A and SEQ ID NO: 10 represents a consensus sequence for Phosphatase box B.

Preferably, the nucleic acid to be introduced into a plant encodes a T6PP protein having at least 80%, 85%, 90%, 95%, 96%, 97%, 98%, 99% or 100% sequence identity to a sequence selected from SEQ ID NOs 1,3,5 and 7. Most preferably, the Class T6PP nucleic acid is as represented by any of SEQ ID NOs 1, 3, 5 and 7.

Examples of proteins useful in the methods of the invention and nucleic acids encoding the same are provided herein in Table A of Example 5.

Also useful in the methods of the invention are homologs of any of the amino acid sequences given in Table A of Example 5. "Homologs" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures) Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company and Table 1 below).

TABLE 1

Examples of Conserved Amino Acid Substitutions

| Residue | Conservative Substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution modifications at predetermined sites in DNA are well known to those skilled in the art and include M13 mutagenesis, T7-Gen in vitro mutagenesis (USB, Cleveland, Ohio), Quick-Change Site Directed mutagenesis (Stratagene, San Diego, Calif.), PCR-mediated site-directed mutagenesis or other site-directed mutagenesis protocols.

Also useful in the methods of the invention are derivatives of any one of the polypeptides given in Table A of Example 5 or orthologs or paralogs of any of the polypeptides given in Table A of Example 5 or derivatives of any orthologs or paralogs of any of the polypeptides given in Table A. "Derivatives" include peptides, oligopeptides, polypeptides which may, compared to the amino acid sequence of the naturally-occurring form of the protein, comprise substitutions of amino acids with non-naturally occurring amino acid residues, or additions of non-naturally occurring amino acid residues. Derivatives of the polypeptides given in Table A of Example 5 are further examples which may be suitable for use in the methods of the invention. Some aspects of the invention involve the modification of residues that affect the activity of the T6PP molecule. In a one embodiment the modification decreases the activity of the T6PP molecule when assayed in vitro. In another aspect the modification lowers the binding affinity of T6PP to its substrate. In another aspect modifications can be made in the active site of the T6PP protein so that the protein's activity is decreased as compared to the T6PP protein without the modification.

"Derivatives" of a polypeptide include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

The invention is illustrated by expressing in a plant various modified T6PP proteins of the T6PP molecule. Surprisingly, these modifications and/or the decreased activity of the T6PP molecules as described herein show increased yield as well as field efficacy in that the plants are healthy and show no adverse phenotypic effects. Performance of the invention is not restricted to these sequences. The methods of the invention may advantageously be performed using any nucleic acid encoding a protein useful in the methods of the invention as defined herein, including nucleic acids encoding orthologs, paralogs and homologs such as (but not limited to) any of the nucleic acid sequences given in Table A of Example 5.

Orthologs and paralogs encompass evolutionary concepts used to describe the ancestral relationships of genes. Paralogs are genes within the same species that have originated through duplication of an ancestral gene and orthologs are genes from different organisms that have originated through speciation, and are also derived from a common ancestral gene.

Orthologs and paralogs may easily be found by performing a so-called reciprocal blast search. Typically, this involves a first BLAST involving BLASTing a query sequence (for example using any of the sequences listed in Table A of Example 5 against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived. The results of the first and second BLASTs are then compared. A paralog is identified if a high-ranking hit from the first blast is from the same species as from which the query sequence is derived, a BLAST back then ideally results in the query sequence amongst the highest hit; an ortholog is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbor joining tree, to help visualize clustering of related genes and to identify orthologs and paralogs.

Table A of Example 5 gives examples of orthologs and paralogs of the T6PP proteins represented by SEQ ID NO 2, 4, 6 and 8. Further orthologs and paralogs may readily be identified using the BLAST procedure described above.

The proteins of the invention are identifiable by the presence of the conserved Trehalose-PPase domain(s). The term "domain" refers to a set of amino acids conserved at specific positions along an alignment of sequences of evolutionarily related proteins. While amino acids at other positions can vary between homologs, amino acids that are highly conserved at specific positions indicate amino acids that are essential in the structure, stability or activity of a protein. Identified by their high degree of conservation in aligned sequences of a family of protein homologs, they can be used as identifiers to determine if any polypeptide in question belongs to a previously identified polypeptide family (in this case, the proteins useful in the methods of the invention and nucleic acids encoding the same as defined herein). In a preferred embodiment of the invention one or more modifications may be introduced into these highly conserved domains to decrease the activity of a particular T6PP protein thus conferring when expressed in a plant increased yield.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases also exist for the identification of domains, for example, SMART (Schultz et al. (1998) Proc. Natl. Acad. Sci. USA 95, 5857-5864; Letunic et al. (2002)

Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788(2003)).

Domains may also be identified using routine techniques, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologs may readily be identified using, for example, the ClustalW multiple sequence alignment algorithm (version 1.83), with the default pair wise alignment parameters, and a scoring method in percentage. Global percentages of similarity and identity may also be determined using one of the methods available in the MatGAT software package (Campanella et al., BMC Bioinformatics. July 2003 10;4:29. MatGAT: an application that generates similarity/identity matrices using protein or DNA sequences.). Minor manual editing may be performed to optimize alignment between conserved motifs, as would be apparent to a person skilled in the art. Furthermore, instead of using full-length sequences for the identification of homologs, specific domains (such as the Trehalose-PPase domain, or one of the motifs defined above) may be used as well.

Furthermore, T6PP proteins (at least in their native form) typically have trehalose-6-phosphate phosphatase activity. Polypeptides with trehalose-6-phosphate phosphatase activity belong to the enzymatic class of EC: 3.1.3.12, according to the classification of the Enzyme Commission of the Nomenclature Committee of the International Union of Biochemistry and Molecular Biology (NC-IUBMB). Enzymes in class EC: 3.1.3.12 catalyze the reaction: trehalose-6-phosphate+$H_2O$=trehalose+phosphate. It is contemplated that any T6PP or protein having T6PP activity can be modified for decreased activity via methods such as point modification(s), irradiation, etc to confer the positive effects as described herein when expressed transgenically in a plant.

The activity of a trehalose-6-phosphate phosphatase protein may be measured by determining the levels of the substrate processed and the levels of product accumulated in an in vitro reaction, that is, by determining the level of trehalose-6-phosphate consumption and/or trehalose accumulation from the reaction. Enzymatic methods to measure trehalose can be based on hydrolyzing trehalose to glucose, such as those described by Van Dijck et al. Biochem J. August 2002 15;366(Pt 1):63-71 and Zentella et al. Plant Physiol. April 1999;119(4):1473-82.

Trehalose-6-phosphate levels may also be measured by HPLC (High Performance Liquid Chromatography) methods as described by Avonce et al. Plant Physiol. November 2004; 136(3):3649-59; Schluepmann et al. 2003. Alternative methods based on determining the release of inorganic phosphate from trehalose-6-phosphate have also been described Klutts et al. J Biol Chem. January 2003 24;278(4):2093-100. An alternative method to determine trehalose-6-phosphate levels using liquid chromatography coupled to MS-Q3 (triple quadrupole MS) has been described by Lunn et al. Biochem J. July 2006 1;397(1):139-48.

Examples of nucleic acids suitable for use in performing the methods of the invention include the nucleic acid sequences given in Table A of Example 5, but are not limited to those sequences. Nucleic acid variants may also be useful in practicing the methods of the invention. Examples of such nucleic acid variants include portions of nucleic acids encoding a protein useful in the methods of the invention, nucleic acids hybridizing to nucleic acids encoding a protein useful in the methods of the invention, splice variants of nucleic acids encoding a protein useful in the methods of the invention, allelic variants of nucleic acids encoding a protein useful in the methods of the invention and variants of nucleic acids encoding a protein useful in the methods of the invention that are obtained by gene shuffling. The terms portion, hybridizing sequence, splice variant, allelic variant and gene shuffling will now be described.

Nucleic acids encoding proteins useful in the methods of the invention need not be full-length nucleic acids, since performance of the methods of the invention does not rely on the use of full-length nucleic acid sequences. Portions useful in the methods of the invention, encode a polypeptide falling within the definition of a nucleic acid encoding a protein useful in the methods of the invention as defined herein. Preferably, the portion is a portion of any one of the nucleic acids given in Table A of Example 5. The portion is typically at least 625 consecutive nucleotides in length, preferably at least 825 consecutive nucleotides in length, or at least 1025 consecutive nucleotides in length or at least 1125 consecutive nucleotides in length, the consecutive nucleotides being of any one of the nucleic acid sequences given in Table A of Example 5 in combination with suggested modification(s) disclosed herein that will decrease the activity of the relative T6PP protein compared the same T6PP not having one or more modifications. In one aspect of the invention the portion is a portion of the nucleic acid of SEQ ID NO: 1. Preferably, the portion encodes an amino acid sequence which when used in the construction of a T6PP/T6PS phylogenetic tree, tends to cluster with the group of T6PP proteins comprising the amino acid sequence represented by SEQ ID NO: 2 rather than with any other group.

A portion of a nucleic acid encoding a T6PP protein as defined herein may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the T6PP protein portion. It is also contemplated that T6PP molecules having no T6PP activity may confer a yield increase when expressed transgenically in a plant.

According to the present invention, there is provided a method for enhancing yield-related traits in plants, particularly increasing seed yield, comprising introducing and expressing in a plant a portion of any one of the nucleic acid sequences given in Table A of Example 5, or a portion of a nucleic acid encoding an ortholog, paralog or homologue of any of the amino acid sequences given in Table A of Example 5 wherein the proteins have been modified in a way to decrease the T6PP protein activity.

Another nucleic acid variant useful in the methods of the invention is a nucleic acid capable of hybridizing under reduced stringency conditions, preferably under stringent conditions, with a nucleic acid encoding a T6PP protein as defined herein, or with a portion as defined herein. In a preferred aspect the T6PP protein will be modified to have decreased activity as compared to a un-modified version of the same T6PP protein thus conferring any one of the following in a transgenic plant increased yield, increased biomass, increased tolerance to abiotic and biotic stress, increased plant vigor, increased sugar, increased oil content, increased seed weight, increased root growth, increased water use efficiency, increased drought tolerance, increased resistance to lodging, increased nutrient use efficiency (e.g. nitrogen) and faster plant development.

Hybridizing sequences useful in the methods of the invention, encode a polypeptide having a Trehalose-PPAse domain and having substantially the same biological activity as T6PP proteins represented by any of the amino acid sequences given in Table A of Example 5. The hybridizing sequence is typically at least 625 consecutive nucleotides in length, preferably at least 825 consecutive nucleotides in length, more preferably at least 1025 consecutive nucleotides in length and most preferably at least 1125 consecutive nucleotides in length, the consecutive nucleotides being of any one of the nucleic acid sequences given in Table A of Example 5. Preferably, the hybridizing sequence is one that is capable of hybridizing to any of the nucleic acids given in Table A of Example 5, or to a portion of any of these sequences, a portion being as defined above. Most preferably, the hybridizing sequence is capable of hybridizing to a nucleic acid as represented by SEQ ID NO: 1 or to a portion thereof. In another preferred aspect the sequence comprises at least one modification that decreases the activity of the relative T6PP protein.

Preferably, the hybridizing sequence encodes an amino acid sequence which when used in the construction of a T6PP/T6PS phylogenetic tree, tends to cluster with the group of T6PP proteins comprising the amino acid sequence represented by SEQ ID NO: 2 rather than with any other group.

Most preferably, the isolated polynucleotide molecule is capable of hybridizing under stringent conditions to a sequence represented by one of SEQ ID NOs 1, 3, 5 and 7.

According to the present invention, there is provided a method for enhancing yield-related traits in plants, particularly increasing seed yield, comprising introducing and expressing in a plant a nucleic acid capable of hybridizing to any one of the nucleic acids given in Table A of Example 5, or comprising introducing and expressing in a plant a nucleic acid capable of hybridizing to a nucleic acid encoding an ortholog, paralog or homologue of any of the nucleic acid sequences given in Table A of Example 5 wherein the sequence has been modified in a way to decrease the T6PP activity of the encoded protein.

Another nucleic acid variant useful in the methods of the invention is a splice variant encoding a T6PP protein as defined hereinabove. The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained or decreased in many aspects of the invention; this may be achieved by selectively retaining or deleting functional segments of the protein. Such splice variants may be found in nature or may be manmade. Methods for predicting and isolating such splice variants are well known in the art (see for example Foissac and Schiex, BMC Bioinformatics. 2005; 6: 25).

According to the present invention, there is provided a method for enhancing yield-related traits in plants, particularly increasing seed yield, comprising introducing and expressing in a plant a splice variant of any one of the nucleic acid sequences given in Table A of Example 5, or a splice variant of a nucleic acid encoding an ortholog, paralog or homologue of any of the amino acid sequences given in Table A of Example 5 wherein these molecules are further modified to have decreased activity.

Preferred splice variants are splice variants of a nucleic acid represented by SEQ ID NO: 1 or a splice variant of a nucleic acid encoding an ortholog or paralog of SEQ ID NO: 2. Preferably, the amino acid sequence encoded by the splice variant comprises any one or more of the motifs or domains as defined herein. Preferably, the amino acid sequence encoded by the splice variant, when used in the construction of a T6PP/T6PS phylogenetic tree, tends to cluster with the group of Class T6PP proteins comprising the amino acid sequence represented by SEQ ID NO: 2 rather than with any other group.

Another nucleic acid variant useful in performing the methods of the invention is an allelic variant of a nucleic acid encoding a T6PP protein as defined hereinabove. Alleles or allelic variants are alternative forms of a given gene, located at the same chromosomal position. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms. The allelic variants useful in the methods of the present invention have substantially the same biological activity as the T6PP protein of SEQ ID NO: 2 and may be mutated at positions within the protein that are correlated to any one of substrate binding, enzyme activity, secondary or tertiary structure.

According to the present invention, there is provided a method for enhancing yield-related traits in plants, particularly increasing seed yield, comprising introducing and expressing in a plant an allelic variant of any one of the nucleic acids given in Table A of Example 5, or comprising introducing and expressing in a plant an allelic variant of a nucleic acid encoding an ortholog, paralog or homologue of any of the amino acid sequences given in Table A of Example 5.

Preferably, the allelic variant is an allelic variant of SEQ ID NO: 1, 3, 5 or an allelic variant of a nucleic acid encoding an ortholog or paralog of SEQ ID NO: 2. Preferably, the amino acid sequence encoded by the allelic variant comprises any one or more of the motifs or domains as defined herein. Preferably, the amino acid sequence encoded by the allelic variant, when used in the construction of a T6PS/T6PP phylogenetic tree, tends to cluster with the group of Class T6PP proteins comprising the amino acid sequence represented by SEQ ID NO: 2, rather than with any other group.

A further nucleic acid variant useful in the methods of the invention is a nucleic acid variant obtained by gene shuffling. Gene shuffling or directed evolution may also be used to generate variants of nucleic acids encoding T6PP proteins with decreased activity as defined above. This consists of iterations of DNA shuffling followed by appropriate screening and/or selection to generate variants of nucleic acids or portions thereof encoding T6PP proteins as defined above having a modified (decreased) biological activity (Castle et al., (2004) Science 304(5674): 1151-4; U.S. Pat. Nos. 5,811, 238 and 6,395,547).

According to the present invention, there is provided a method for enhancing yield-related traits in plants, comprising introducing and expressing in a plant a variant of any one of the nucleic acid sequences given in Table A of Example 5, or comprising introducing and expressing in a plant a variant of a nucleic acid encoding an ortholog, paralog or homologue of any of the amino acid sequences given in Table A of Example 5, which variant nucleic acid is obtained by gene shuffling. In a preferred embodiment, one would screen for T6PPs having a lower rate of substrate binding and/or activity.

Preferably, the variant nucleic acid obtained by gene shuffling encodes an amino acid sequence comprising any one or more of the motifs or domains as defined herein. Preferably, the amino acid encoded sequence by the variant nucleic acid obtained by gene shuffling, when used in the construction of a T6PS/T6PP phylogenetic tree, tends to cluster with the group of T6PP proteins comprising the amino acid sequence represented by SEQ ID NO: 2 rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds.). One aspect of the invention is to employ site-directed mutagenesis so to decrease the T6PP protein's ability to bind with its substrate.

Nucleic acids encoding T6PP proteins may be derived from any natural or artificial source. The nucleic acid may be modified from its native form in composition and/or genomic environment through deliberate human manipulation. Preferably the T6PP-encoding nucleic acid is from a plant, further preferably from a monocotyledonous plant, more preferably from the Oryza family, most preferably the nucleic acid is from rice.

The present invention also encompasses plants or parts thereof (including seeds) obtainable by the methods according to the present invention. The plants or parts thereof comprise a nucleic acid transgene encoding a T6PP protein that has been intentionally or non-intentionally modified to have decreased activity.

The invention also provides hitherto unknown T6PP nucleic acid sequences and T6PP protein sequences that may be modified as described herein for methods of conferring increased yield in a plant. These sequences may also be useful in performing the methods of the invention.

According to a further embodiment of the present invention, there is therefore provided an isolated nucleic acid molecule comprising:
  (i) a nucleic acid represented by SEQ ID NO: 1, SEQ ID NO: 3 or SEQ ID NO: 5;
  (ii) the complement of any one of the SEQ ID NOs given in (i);
  (iii) a nucleic acid encoding a T6PP protein having, in increasing order of preference, at least 80%, 85%, 90%, 95%, 96%, 97%, 98%, 99% or 100% sequence identity to any one of the amino acid sequences given in SEQ ID 2, SEQ ID NO: 4, or SEQ ID NO: 6.
  (iv) a nucleic acid capable of hybridizing under stringent conditions to any one of the nucleic acids given in (i), (ii) or (iii) above.

According to a further embodiment of the present invention, there is also provided an isolated polypeptide comprising:
  (i) an amino acid sequence represented by any one of SEQ ID NO: 2, SEQ ID NO: 4, or SEQ ID NO: 6;
  (ii) an amino acid sequence having, in increasing order of preference, at least at least 80%, 85%, 90%, 95%, 96%, 97%, 98%, 99% or 100% sequence identity to any one of the amino acid sequences given in SEQ ID NO: 2, SEQ ID NO: 4, or SEQ ID NO: 6;
  (iii) derivatives of any of the amino acid sequences given in (i) or (ii) above.

The invention also provides genetic constructs, expression cassettes and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in transformed cells. The invention also provides use of a gene construct as defined herein in the methods of the invention.

The invention also provides a construct comprising:
  (i) nucleic acid encoding T6PP protein as defined above;
  (ii) one or more control sequences capable of driving expression of the nucleic acid sequence of (a); and optionally
  (iii) a transcription termination sequence.

Preferably the nucleic acid in the construct according to the invention is a polynucleotide molecule encoding a T6PP protein with an amino acid sequence in increasing order of preference of at least 80%, 85%, 90%, 95%, 96%, 97%, 98%, 99% or 100% sequence identity to a sequence represented by one of SEQ ID NO: 1, SEQ ID NO: 3, and SEQ ID NO: 5. Most preferably, the T6PP polynucleotide molecule is any of the nucleotide sequences of SEQ ID NO: 1, SEQ ID NO: 3, and SEQ ID NO: 5.

Plants are transformed with a vector comprising the sequence of interest (i.e., a nucleic acid encoding a T6PP polypeptide that has been intentionally or non-intentionally modified to have decreased activity). The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognizing and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a—35 box sequence and/or—10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The term "promoter" refers to a nucleic acid control sequence located upstream from the transcriptional start of a gene and which is involved in recognizing and binding of RNA polymerase and other proteins, thereby directing transcription of an operably linked nucleic acid. A "plant promoter" comprises regulatory elements, which mediate the expression of a coding sequence segment in plant cells. Accordingly, a plant promoter need not be of plant origin, but may originate from viruses or microorganisms, for example from viruses which attack plant cells. The "plant promoter" can also originate from a plant cell, e.g. from the plant which is transformed with the nucleic acid sequence to be expressed. This also applies to other " plant" regulatory signals, such as " plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule is operably to a suitable promoter.

The promoter may be a constitutive promoter, which refers to a promoter that is transcriptionally active during most, but not necessarily all, phases of its growth and development and under most environmental conditions, in at least one cell, tissue or organ. Alternatively, the promoter may be an inducible promoter, i.e. having induced or increased transcription initiation in response to a chemical (for a review see Gatz 1997, Annu. Rev. Plant Physiol. Plant Mol. Biol., 48:89-108), environmental or physical stimulus. Another example of an inducible promoter is a stress-inducible promoter, i.e. a promoter activated when a plant is exposed to various stress conditions, or a pathogen-induced promoter.

Additionally or alternatively, the promoter may be an organ-specific or tissue-specific promoter, i.e. one that is capable of preferentially initiating transcription in certain organs or tissues, such as the leaves, roots, seed tissue etc.; or the promoter may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain organs or tissues only are referred to herein as "organ-specific" or "tissue-specific" respectively, similarly, promoters able to initiate transcription in certain cells only are referred to herein as "cell-specific".

In one aspect of the invention, the T6PP nucleic acid or variant thereof is operably linked to a promoter that directs expression of the T6PP to plant maternal reproductive tissue such as spikelet tissue, bract tissue, spikelet meristem tissue, inflorescence stalk tissue, ear node, and immature floral tissue. Promoters such the OsMADS promoters as described in U.S. Patent Application Publication 2007/0006344 herein incorporated by reference may be used in certain aspects of the invention.

For the identification of functionally equivalent promoters, the promoter strength and/or expression pattern of a candidate promoter may be analyzed for example by operably linking the promoter to a reporter gene and assay the expression level and pattern of the reporter gene in various tissues of the plant. Suitable well-known reporter genes include for example β-glucuronidase or β-galactosidase. The promoter activity is assayed by measuring the enzymatic activity of the β-glucuronidase or β-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally, the term "weak promoter" refers to a promoter that drives expression of a coding sequence at a low level, levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1,000 transcripts per cell.

It is contemplated that regulatory elements may be used to modulate the duration for which a given trait is present. For instance, one may construct expression cassettes to express a modified T6PP during plant flowering thus conferring drought tolerance for this stage of development of the plant. Likewise, one may also construct expression cassettes that constitutively expresses a modified T6PP in a plant thus, not to be limited by theory, confers drought tolerance throughout the plant's lifecycle.

Optionally, one or more terminator sequences may be used in the construct introduced into a plant. The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5'-untranslated region (UTR)) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994). In some aspects of the invention, one may wish to increase the expression of a T6PP modified to have decrease substrate binding capabilities in a plant to confer increased yield.

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. As used herein, the term "selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xlose isomerase for the utilization of xylose, or antinutritive markers such as the resistance to 2-deoxyglucose). Expression of visual marker genes results in the formation of color (for example β-glucuronidase, GUS or β-galactosidase with its colored substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems, which have the advantage that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The invention also provides a method for the production of transgenic plants having enhanced yield-related traits, particularly increased seed yield, relative to control plants, comprising introduction and expression in a plant of any nucleic acid encoding a T6PP protein as defined hereinabove.

One aspect of the invention provides expression cassettes comprising:
(a) the nucleic acid sequences encoding proteins useful in the methods of the invention, or
(b) genetic control sequence(s) which is operably linked with the nucleic acid sequence according to the invention, for example a promoter, or
(c) a) and b)

More specifically, the present invention provides a method for the production of transgenic plants having increased yield, which method comprises:

(i) introducing and expressing in a plant, plant part or plant cell a T6PP nucleic acid or variant thereof wherein the T6PP has decreased substrate binding activity; and (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower 55erea155na55. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development cycle, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in Arabidopsis Research. Word Scientific, Singapore, pp. 274-289]. Alternative methods are based on the repeated removal of the inflorescences and incubation of the excision site in the centre of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of Arabidopsis, intact plants under reduced pressure are treated with an agrobacterial suspension [Bechthold, N (1993). C R Acad. Sci. Paris Life Sci., 316: 1194-1199], while in the case of the "floral dip" method the developing floral tissue is incubated briefly with a surfactant-treated agrobacterial suspension [Clough, S J and Bent, A F (1998). The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantage because plastids are inherited maternally in most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. September 2001 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

The genetically modified plant cells can be regenerated via all methods with which the skilled worker is familiar Suitable methods can be found in the abovementioned publications by S. D. Kung and R. Wu, Potrykus or Hagen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a T6PP protein as defined hereinabove. Preferred host cells according to the invention are plant cells.

Host plants for the nucleic acids or the vector used in the method according to the invention, the expression cassette or construct or vector are, in principle, advantageous in all plants, which are capable of synthesizing the polypeptides used in the inventive method.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to one feature of the invention, the modulated expression is increased expression. Methods for increasing expression of nucleic acids or genes, or gene products, are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added as described above. Other control sequences (besides promoter, enhancer, silencer, intron sequences, 3'-UTR and/or 5'-UTR regions, micro-RNA target sites, may be protein and/or RNA stabilizing elements.

As mentioned above, a method for modulating expression of a nucleic acid encoding a T6PP protein modified to have decreased activity is by introducing and expressing in a plant a nucleic acid encoding a T6PP protein; however the effects of performing the method, i.e. enhancing yield-related traits may also be achieved using other well known techniques. A description of some of these techniques will now follow.

One such technique is T-DNA activation tagging (Hayashi et al. Science (1992) 1350-1353), which involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

The effects of the invention may also be reproduced using the technique of TILLING (Targeted Induced Local Lesions In Genomes). This is a mutagenesis technology useful to generate and/or identify a nucleic acid encoding a Class III T6PP protein with modified expression and/or activity. TILLING also allows selection of plants carrying such mutant variants. These mutant variants may exhibit modified expression, either in strength or in location or in timing (if the mutations affect the promoter for example). These mutant variants may exhibit higher Class III T6PP protein activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in Arabidopsis Research, Koncz C, Chua NH, Schell J, eds. Singapore, World Scientific Publishing Co, pp. 16-82; Feldmann et al., (1994) In Meyerowitz E M, Somerville C R, eds, Arabidopsis. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

The effects of the invention may also be reproduced using homologous recombination, which allows introduction in a genome of a selected nucleic acid at a defined selected position. Homologous recombination is a standard technology used routinely in biological sciences for lower organisms such as yeast or the moss Physcomitrella. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Lida and Terada (2004) Cum Opin. Biotech 15(2): 132-8).

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of suitable control plants.

The terms "increase", "improving" or "improve" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to the wild type plant as defined herein.

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigor, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigor. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period) Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a T6PP protein as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects. Another abiotic stress may result from a nutrient deficiency, such as a shortage of nitrogen, phosphorus and potassium.

The methods of the present invention may be performed under non-stress conditions or under conditions of mild drought to confer plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinization are manifested primarily as osmotic stress, resulting in the disruption of homeostasis and ion distribution in the cell. Oxidative stress, which frequently accompanies high or low temperature, salinity or drought stress may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under drought conditions increased yield relative to suitable control plants grown under comparable conditions. Therefore, according to the present invention, there is provided a method for enhancing yield-related traits in plants grown under non-stress conditions or under drought conditions, which method comprises increasing expression in a plant of a nucleic acid encoding a modified T6PP polypeptide having decreased substrate binding and/or activity.

In one embodiment of the invention, the enhanced yield-related trait is manifested as an increase in one or more of the following: total number of seeds per plant, number of filled seeds per plant and seed weight per plant. Preferably, these increases are found in plants grown under non-stress conditions.

The methods of the invention are advantageously applicable to any plant.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising: *Acer* spp., *Actinidia* spp., *Abelmoschus* spp., *Agropyron* spp., 64ereal64na64., *Amaranthus* spp., *Ananas comosus, Annona* spp., *Apium graveolens, Arachis* spp, *Artocarpus* spp., *Asparagus officinalis, Avena* spp. (e.g. *Avena sativa, Avena fatua, Avena* 64ereal64na, *Avena fatua* var. *sativa, Avena* 64ereal), *Averrhoa carambola, Benincasa hispida, Bertholletia excelsea, Beta vulgaris, Brassica* spp. (e.g. *Brassica napus, Brassica rapa* ssp. [canola, oilseed rape, turnip rape]), *Cadaba* 64ereal64n, *Camellia sinensis, Canna indica, Capsicum* spp., *Carex data, Carica papaya, Carissa macrocarpa, Carya* spp., *Carthamus tinctorius, Castanea* spp., *Cichorium endivia, Cinnamomum* spp., *Citrullus lanatus, Citrus* spp., *Cocos* spp., *Coffea* spp., *Colocasia esculenta, Cola* spp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eriobotrya japonica, Eugenia uniflora, Fagopyrum* spp., *Fagus* spp., *Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea* 65ereal65na, *Mangifera indica, Manihot* spp., *Manilkara zapota, Medicago sativa, Melilotus* spp., *Mentha* spp., *Miscanthus* spp., *Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Passiflora edulis, Pastinaca sativa, Persea* spp., *Petroselinum crispum, Phaseolus* spp., *Phoenix* spp., *Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Sambucus* spp., *Secale* 65ereal, *Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The present invention also encompasses use of nucleic acids encoding the T6PP protein described herein and use of these T6PP proteins in enhancing yield-related traits in plants.

Nucleic acids encoding the T6PP protein described herein, or the T6PP proteins themselves, may find use in breeding programs in which a DNA marker is identified which may be genetically linked to a T6PP encoding gene wherein the T6PP protein has decreased activity or substrate binding. The nucleic acids/genes, or the T6PP proteins themselves may be used to define a molecular marker. This DNA or protein marker may then be used in breeding programs to select plants having enhanced yield-related traits as defined hereinabove in the methods of the invention.

Nucleic acids encoding T6PP proteins may also be used as probes for genetically and physically mapping the genes that they are a part of, and as markers for traits linked to those genes. Such information may be useful in plant breeding in order to develop lines with desired phenotypes. Such use of T6PP protein-encoding nucleic acids requires only a nucleic acid sequence of at least 15 nucleotides in length. The Class III T6PP protein-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the T6PP protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the T6PP protein-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154).

Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In one aspect of the invention, not to be limited by theory, the T6PP comprising modifications as described herein have a reduced activity and further form a protein-protein complex with T6PS. Not to be limited by theory, one possible aspect of the invention is the protein-protein T6PP/T6PS complex which may be used to confer in a plant increased yield and increased tolerance to stress. In another aspect, one could modify any T6PP polypeptide having the consensus sequence of SEQ ID NO: 7 to have lower binding affinity to T6P. It is envisioned that in one aspect it may be possible to create or use existing chemicals that may mimic the complex or create orthogonal structures that may be employed to mimic the T6PP/T6PS complex. In one aspect, not to be limited by theory, is that one or more modifications may be carried out in the B-phosphatase Box of any given T6PP protein to confer in a plant increased yield.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

EXAMPLES

Example 1

Identification and Cloning of the Rice T6PP cDNA Sequence into a Binary vector

The first vascular plant trehalose-6-phosphate phosphatase genes were cloned from *Arabidopsis thaliana* by complementation of a yeast T6PS2 deletion mutant (Vogel et al. 1998). The genes designated AtT6PPA and AtT6PPB (GenBank accessions AF007778 and AF007779) were shown at that time to have trehalose-6-phosphate phosphatase activity. The AtT6PPA and AtTTPB protein sequences were used in TBLASTN queries of maize and rice sequence databases. Sequence alignments organized the hits into individual genes. Three maize and three rice T6PP homologs were identified. The rice T6PP (OsT6PP) cDNA sequence as indicated by SEQ ID NO. 1 was amplified using high-fidelity PCR. The 50 pL reaction mixture consisted of 1 pL rice cDNA library (prepared from callus mRNA in Stratagene's Lambda Unizap Vector, primary library size >1×10$^6$ pfu, amplified library titer >1×10$^{12}$ pfu/mL), 200 µM dNTPs, 1 µL 20 µM of oligonucleotide primer T6PP-EC-5 (5'-catggaccatggatttgagcaat-agctcac-3') and 1 μL 20 μM of oligonucleotide primer T6PP-EC-3 (5'-atcgcagagctcacactgagtgcttcttcc-3'), 5 μL 10× Cloned PFU buffer and 2.5 Units of Pfuturbo DNA polymerase. The thermocycling program was 95° C. for 2 minutes followed by 40 cycles of (94° C. for 15 seconds, 50° C. for 1 minute, 72° C. for 1 minute) followed by 72° C. for 10 minutes. The rice T6PP product was cloned with the Zero Blunt TOPO PCR cloning kit. The pCR-Blunt-II-TOPO-OsT6PP is identified by digesting 5 μL pCR-Blunt-II-TOPO-OsT6PP miniprep DNA with EcoRI in a 20 μL reaction containing 2 μg BSA and 2 μL 10× EcoRI restriction endonuclease buffer. The reaction is incubated at 37° C. for 2 hours and the pCR-Blunt-II-TOPO-OsT6PP (EcoRI) products are resolved on 1% TAE agarose. The pCR-Blunt-II-TOPO-OsT6PP clone is then sequenced. The OsT6PP cDNA is flanked by NcoI/SacI restriction endonuclease sites. The OsT6PP was then further cloned into a binary vector as described in Example 8 of U.S. Patent Application Publication 2007/0006344 (therein referred to OsT6PP-3 and indicated by nucleotide SEQ ID NO: 531 and protein SEQ ID NO: 532)

Example 2

Initial Evaluation of Rice T6PP Maize Events in the Greenhouse

Rice T6PP maize events comprising SEQ ID NO: 1 operably linked to a promoter having preferential expression in maternal reproductive tissue (i.e. OsMADS promoter) were generated and further evaluated in both the greenhouse and field as described in Examples 8-13 in U.S. Patent Application Publication 2007/0006344. Initial greenhouse and field evaluation of the maize events indicated some events having a yield increases in both non-drought and drought conditions (See U.S. Patent Application Publication 2007/0006344 herein incorporated by reference).

Example 3

Evaluation and Identification High Yielding T6PP Maize Events

The maize events shown to confer a yield increase in the trials described in Example 2 and more specifically in U.S. Patent Application Publication 2007/0006344 were further characterized for yield and field efficacy. These events contained either binary construct 15777 or 15769 as is described in U.S. Patent Application Publication 2007/0006344. Essentially binary construct 15769 comprises an expression cassette having an OsT6PP (indicated in SEQ ID NO: 1 of the current application) operably linked to an OsMADS6 promoter (SEQ ID NO: 11). Binary construct 15777 contains the same expression cassette (OsMADS6 promoter and OsT6PP coding sequence) with the addition of transcriptional enhancers upstream of the OsMADS6 promoter. The details and specifics of both these constructs may again be found in the U.S. Patent Application Publication 2007/0006344. Overall there were 645 TO maize events generated from 15769 and 587 maize events were generated comprising the 15777 binary construct. Following the course of generation of transgenic events during plant transformation, selection of events having successfully integrated into the genomic DNA, as well as growth in greenhouse and field conditions relatively a small number of events were carried forward for field trials based on the selection criteria as well as plant event survival and phenotype criteria. The relatively high level of attrition led to only 17 events showing field efficacy. Events derived from maize plants comprising the 15777 binary construct proved to be most efficacious in the field testing. Two events (herein referred to as "Event 1" and "Event 2") were selected based upon viability and performance in managed stress environments (yield preservation under drought at flowering) and in agronomic trials which measured yield. Overall, best performing events comprising construct 15777 demonstrated a significant bushel per acre yield advantage over control check samples and other events.

Example 4

Event 1 and 2 Sequence Analysis

Event 1 and event 2 were further analyzed by sequencing of the T6PP CDS. PCR was used to amplify the integrated OsT6PP coding sequence using primers which anneal to the 5' and 3' region of the coding sequence. The respective PCR amplicons resulted in the approximate 1.1 Kb band size as would be expected from the coding sequence of the OsT6PP as depicted in SEQ ID NO: 1 which was the sequence that was comprised in the relative expression cassette. The amplicons were further sequenced as is well established in the art. Sequencing data indicated that both events (1 and 2) contained modifications. Event 1 contained a single point modification at nucleotide 730 respective to SEQ ID NO: 1 (T*CATTA where * indicates point of modification). This single modification led to an amino acid modification at residue 244 relative to SEQ ID NO: 2 changing a His residue to an Asp residue as is represented in SEQ ID NO: 3 herein interchangeably referred to as the "T6PP single modification". Event 2 was found to contain two modifications at nucleotides 305 (TG*CTTCC where * indicates point of modification) and 388 (CGCC*ATT where * indicates point of modification) respective to SEQ ID NO: 1. The two point nucleotide modifications identified in Event 2 resulted in a change from Ala to Val at position 102 and Ile changed to Phe at position 129 or the T6PP polypeptide as represented by SEQ ID NO: 5 herein interchangeably referred to as the "T6PP double modification". Interestingly, as shown in subsequent Examples, two of these modifications are located in highly conserved domains of the T6PP protein. The Ala to Val at position 102 falls outside of the highly conserved regions. These highly conserved domains are involved in substrate binding and/or protein-protein interactions when forming a complex.

Example 5

Identification of T6PPs having Similar Homology and Function that may be Improved through the Introduction of Modifications Sequences (full length cDNA, ESTs or genomic) related to SEQ ID NO: 1 and/or protein sequences related to SEQ ID NO: 2 can be identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program can be used to find regions of local similarity between sequences by comparing nucleic acid or polypeptide sequences to sequence databases and by calculating the statistical significance of matches. The polypeptide encoded by SEQ ID NO: 1 may be used with the TBLASTN algorithm, with default settings and the filter to ignore low complexity sequences set off. The output of the analysis may be viewed by pair-wise comparison, and ranked according to the probability score (E-value), where the score reflects the probability that a particular alignment occurs by chance (the lower the E-value, the more significant the hit). In addition to E-values, comparisons may also be scored by percentage identity. Percentage identity refers to the number of identical nucleotides (or amino acids) between the two compared nucleic acid (or polypeptide) sequences over a particular length. In some instances, the default parameters can be adjusted to modify the stringency of the search.

Table A provides a list of nucleic acid and protein sequences related to the nucleic acid sequence as represented by SEQ ID NO: 1 and the protein sequence represented by SEQ ID NO: 2 that may be useful in various aspects of the invention. Sequences were indicated through sequence homology search as well as T6PP molecules indicated in the art.

TABLE A

| NAME | SOURCE ORGANISM | nt/pt | SEQ ID NO: | DATABASE ACCESSION NO. |
|---|---|---|---|---|
| SEQ ID NO: 1 | *Oryza sativa* | nt | 1 | N/A |
| SEQ ID NO: 2 | *Oryza sativa* | pt | 2 | N/A |
| SEQ ID NO: 3 | *Oryza sativa* | nt | 3 | N/A |
| SEQ ID NO: 4 | *Oryza sativa* | pt | 4 | N/A |
| SEQ ID NO: 5 | *Oryza sativa* | nt | 5 | N/A |
| SEQ ID NO: 6 | *Oryza sativa* | pt | 6 | N/A |
| AT1G22210 | *Arabidopsis thaliana* | nt | N/A | AT1G22210 |
| AT1G22210 | *Arabidopsis thaliana* | pt | N/A | AT1G22210 |
| AT1G35910 | *Arabidopsis thaliana* | nt | N/A | AT1G35910 |
| AT1G35910 | *Arabidopsis thaliana* | pt | N/A | AT1G35910 |
| AT1G78090 | *Arabidopsis thaliana* | nt | N/A | AT1G78090 |
| AT1G78090 | *Arabidopsis thaliana* | pt | N/A | AT1G78090 |
| AT2G22190 | *Arabidopsis thaliana* | nt | N/A | AT2G22190 |
| AT2G22190 | *Arabidopsis thaliana* | pt | N/A | AT2G22190 |
| AT4G12430 | *Arabidopsis thaliana* | nt | N/A | AT4G12430 |
| AT4G12430 | *Arabidopsis thaliana* | pt | N/A | AT4G12430 |
| AT4G22590 | *Arabidopsis thaliana* | nt | N/A | AT4G22590 |
| AT4G22590 | *Arabidopsis thaliana* | pt | N/A | AT4G22590 |
| At4g39770 | *Arabidopsis thaliana* | nt | N/A | At4g39770 |
| At4g39770 | *Arabidopsis thaliana* | pt | N/A | At4g39770 |
| AT5G10100 | *Arabidopsis thaliana* | nt | N/A | AT5G10100 |
| AT5G10100 | *Arabidopsis thaliana* | pt | N/A | AT5G10100 |
| AT5G51460 | *Arabidopsis thaliana* | nt | N/A | AT5G51460 |
| AT5G51460 | *Arabidopsis thaliana* | pt | N/A | AT5G51460 |
| AT5G65140 | *Arabidopsis thaliana* | nt | N/A | AT5G65140 |
| AT5G65140 | *Arabidopsis thaliana* | pt | N/A | AT5G65140 |
| pOP-lcl\|scaff__II.875 | *Populus trichocarpa* | nt | N/A | pOP-lcl\|scaff__II.875 |
| pOP-lcl\|scaff__II.875 | *Populus trichocarpa* | pt | N/A | pOP-lcl\|scaff__II.875 |
| pOP-lcl\|scaff__V.739 | *Populus trichocarpa* | nt | N/A | pOP-lcl\|scaff__V.739 |
| pOP-lcl\|scaff__V.739 | *Populus trichocarpa* | pt | N/A | pOP-lcl\|scaff__V.739 |
| pOP-lcl\|scaff__VII.559 | *Populus trichocarpa* | nt | N/A | pOP-lcl\|scaff__VII.559 |
| pOP-lcl\|scaff__VII.559 | *Populus trichocarpa* | pt | N/A | pOP-lcl\|scaff__VII.559 |
| pOP-lcl\|scaff__127.52 | *Populus trichocarpa* | nt | N/A | pOP-llcl\|scaff__127.52 |
| pOP-lcl\|scaff__127.52 | *Populus trichocarpa* | pt | N/A | pOP-llcl\|scaff__127.52 |
| pOP-lcl\|scaff__III.843 | *Populus trichocarpa* | nt | N/A | pOP-llcl\|scaff__III.843 |
| pOP-lcl\|scaff__III.843 | *Populus trichocarpa* | pt | N/A | pOP-llcl\|scaff__III.843 |
| pOP-lcl\|scaff__V.167 | *Populus trichocarpa* | nt | N/A | pOP-llcl\|scaff__V.167 |
| pOP-lcl\|scaff__V.167 | *Populus trichocarpa* | pt | N/A | pOP-llcl\|scaff__V.167 |
| pOP-lcl\|scaff__XII.1254 | *Populus trichocarpa* | nt | N/A | pOP-llcl\|scaff__XII.1254 |
| pOP-lcl\|scaff__XII.1254 | *Populus trichocarpa* | pt | N/A | pOP-llcl\|scaff__XII.1254 |
| pOP-lcl\|scaff__XV.1052 | *Populus trichocarpa* | nt | N/A | pOP-llcl\|scaff__XV.1052 |
| pOP-lcl\|scaff__XV.1052 | *Populus trichocarpa* | pt | N/A | pOP-llcl\|scaff__XV.1052 |
| Os02g0661100 | *Oryza sativa* | nt | N/A | Os02g0661100 |
| Os02g0661100 | *Oryza sativa* | pt | N/A | Os02g0661100 |
| Os02g0753000 | *Oryza sativa* | nt | N/A | Os02g0753000 |
| Os02g0753000 | *Oryza sativa* | pt | N/A | Os02g0753000 |
| Os03g0386500 | *Oryza sativa* | nt | N/A | Os03g0386500 |
| Os03g0386500 | *Oryza sativa* | pt | N/A | Os03g0386500 |
| Os06g0222100 | *Oryza sativa* | nt | N/A | Os06g0222100 |
| Os06g0222100 | *Oryza sativa* | pt | N/A | Os06g0222100 |
| Os07g0485000 | *Oryza sativa* | nt | N/A | Os07g0485000 |
| Os07g0485000 | *Oryza sativa* | pt | N/A | Os07g0485000 |
| Os07g0624600 | *Oryza sativa* | nt | N/A | Os07g0624600 |
| Os07g0624600 | *Oryza sativa* | pt | N/A | Os07g0624600 |
| Os09g0369400 | *Oryza sativa* | nt | N/A | Os09g0369400 |
| Os09g0369400 | *Oryza sativa* | pt | N/A | Os09g0369400 |
| Os10g0553300 | *Oryza sativa* | nt | N/A | Os10g0553300 |
| Os10g0553300 | *Oryza sativa* | pt | N/A | Os10g0553300 |
| Aquilegia_TC11239 | *Aquilegia* ssp | nt | N/A | Aquilegia_TC11239 |
| Aquilegia_TC11239 | *Aquilegia* ssp | pt | N/A | Aquilegia_TC11239 |
| Aquilegia_TC17706 | *Aquilegia* ssp | nt | N/A | Aquilegia_TC17706 |
| Aquilegia_TC17706 | *Aquilegia* ssp | pt | N/A | Aquilegia_TC17706 |
| Bc_Q4AC11 | *Brassica campestris* | nt | N/A | Bc_Q4AC11 |
| Bc_Q4AC11 | *Brassica campestris* | pt | N/A | Bc_Q4AC11 |

TABLE A-continued

| NAME | SOURCE ORGANISM | nt/pt | SEQ ID NO: | DATABASE ACCESSION NO. |
|---|---|---|---|---|
| Br_Q4ABQ9 | Brassica rapa | nt | N/A | Br_Q4ABQ9 |
| Br_Q4ABQ9 | Brassica rapa | pt | N/A | Br_Q4ABQ9 |
| Gh_TC35369 | Gossypium_hirsutum | nt | N/A | Gh_TC35369 |
| Gh_TC35369 | Gossypium_hirsutum | pt | N/A | Gh_TC35369 |
| Hv_TC139314 | Hordeum vulgare | nt | N/A | HV_TC139314 |
| Hv_TC139314 | Hordeum vulgare | pt | N/A | HV_TC139314 |
| Mt_TC108059 | Medicago_truncatula | nt | N/A | Mt_TC108059 |
| Mt_TC108059 | Medicago_truncatula | pt | N/A | Mt_TC108059 |
| Mt_TC108097 | Medicago_truncatula | nt | N/A | Mt_TC108097 |
| Mt_TC108097 | Medicago_truncatula | pt | N/A | Mt_TC108097 |
| Nb_TC7464 | Nicotiana benthamiana | nt | N/A | Nb_TC7464 |
| Nb_TC7464 | Nicotiana benthamiana | pt | N/A | Nb_TC7464 |
| Nt_Q3ZTF5 | Nicotiana tabacum | nt | N/A | Nt_Q3ZTF5 |
| Nt_Q3ZTF5 | Nicotiana tabacum | pt | N/A | Nt_Q3ZTF5 |
| Nt_TC7310 | Nicotiana tabacum | nt | N/A | Nt_TC7310 |
| Nt_TC7310 | Nicotiana tabacum | pt | N/A | Nt_TC7310 |
| Sb_TC17204 | Sorghum_bicolor | nt | N/A | Sb_TC17204 |
| Sb_TC17204 | Sorghum_bicolor | pt | N/A | Sb_TC17204 |
| St_TC151769 | Solanum_tuberosum | nt | N/A | St_TC151769 |
| St_TC151769 | Solanum_tuberosum | pt | N/A | St_TC151769 |
| Ta_TC252250 | Triticum_aestivum | nt | N/A | Ta_TC252250 |
| Ta_TC252250 | Triticum_aestivum | pt | N/A | Ta_TC252250 |
| Zm_ABD92779 | Zea mays | nt | N/A | Zm_ABD92779 |
| Zm_ABD92779 | Zea mays | pt | N/A | Zm_ABD92779 |
| Zm_ABD92780 | Zea mays | nt | N/A | Zm_ABD92780 |
| Zm_ABD92780 | Zea mays | pt | N/A | Zm_ABD92780 | nt = nucleotide
pt = protein
N/A = Not applicable

Following identification of the T6PPs listed in Table A, these T6PPs were next aligned with SEQ ID NOS: 1, 3, and 5 (using Vector NTI alignment tools by INVITROGEN Inc) to determine whether or not the modifications are occurring in conserved regions of the protein. There is a high amount of conserved sequence across the various T6PP proteins as indicated by the consensus sequence as depicted in SEQ ID NO: 7. Below is the consensus sequence followed by comments that can be used to modify any of the T6PP nucleotides and/or proteins listed in Table A, so that when employed in a transgenic plant, will result in increased yield and/or increase tolerance to stress as well as show efficacy in the field. It is also contemplated that any protein having a consensus sequence comprising 50%, 60%, 70%, 80%, 90%, 95%, 99% or 100% sequence identity to SEQ ID NO: 7 may be modified as described herein and expressed in plants as described herein.

```
Consensus Sequence (as Depicted in SEQ ID NO: 7):
MXXXXXVVXDXXXXXXXXXXXXXXXXXXXXXXXXXXXXXXXXXXXXX

XXXXXXXXXXXXXXXXXXXXXXRXXGWVDSMRASSPTRXKXXXXXXXX

XXSEXXDXXXSXXXXXXXXXXXXXXXXXXXXXXXXXXXXXLKHPSALX

XFEXIVXAAKGKQIYMFLDYDGTLSPIVDDPDRAFMSDXMRXXXXXXXX

XXXXXXXXXXXXXXXXXXXXAVRXYAKYFPTAIVSGRCRDKVYXFVKLXEL

YYAGSHGMDIKGPAKXXXXXXXXXXXXXXXXXKXXXXXXVLFQPASEFL

PMIDEVYKXLVEKTKXXIPGAKVENNKFCVSVHFRCVDEKXWXXLAXXVR

SVLKEYPKLRLTQGRKVLEIRPXIKWDKGKALEFLLESLGFAXXXXXXXX

XNXXDVLPIYIGDDRTDEDAFKVLRERGQXXGFGILVSKXPKETXASYSL

QDPSEVMEXXXXXXXXXXXXXXXXXXXXXFLXRLVXWKKXS
```

The consensus sequence displays the highly conserved residues present across the multiple T6PP polypeptides listed in Table A. It is also contemplated that this consensus sequence would also be applicable to other T6PPs not listed in Table A. The "X" marked positions in the consensus sequence above indicates regions of variability wherein any other single letter refers to the common single letter amino acid notation commonly used in the art. The underlined amino acid residues indicate regions that may be modified to construct T6PP polypeptides that confer increased yield and/or increased stress resistance in a transgenic plant. In one aspect any one of the residues DYDGTLSPIV (SEQ ID NO: 12) which encode a B-phosphatase box may be modified to confer proteins that when expressed in a plant may confer increased yield and/or increased tolerance to stress. In an embodiment of the invention the I (Isoleucine) in the amino acid sequence encoding a B-phosphatase box "DYDGTLSPIV" from the consensus sequence above is changed to an F (Phenylalanine) to encode (DYDGTLSPFV) (SEQ ID NO: 13). In another embodiment the "X" in the consensus sequence above is a V (Valine), which is a change from Alanine in the original sequence. This change is outside of a conserved domain and may not affect enzyme activity. Another embodiment would include altering the "H" (Histidine) within the "CVSVHFRCV" (SEQ ID NO: 14) of the consensus sequence above, is changed to a D (Aspartic Acid) altering the consensus sequence to the sequence "CVSVDFRCV" (SEQ ID NO: 15). It is contemplated that any modification to at least one conserved amino acid residue of SEQ ID NO: 7 wherein the modification results in a decrease in T6PP activity may be expressed in a plant to confer increased yield in stress and non-stress conditions.

Although the foregoing invention has been described in some detail by way of illustration and example for purposes of clarity and understanding, it will be clear to those of skill in the art that certain changes and modifications may be practiced within the scope of the appended claims.

What is claimed is:

1. A polynucleotide encoding a trehalose-6-phosphate phosphatase polypeptide, wherein the polypeptide comprises SEQ ID NO: 4 or SEQ ID NO: 6.

2. A maize plant, plant cell, plant part or plant sample comprising the polynucleotide of claim 1.

3. A maize host cell comprising the polynucleotide of claim 1.

4. A maize plant sample comprising the polynucleotide of claim 1.

5. A binary vector or expression cassette comprising the polynucleotide of claim 1.

6. An expression cassette comprising a polynucleotide operably linked to a promoter that controls transcription of said polynucleotide wherein said polynucleotide encodes a trehalose-6-phosphate phosphatase polypeptide, wherein the polypeptide comprising SEQ ID NO: 4 or SEQ ID NO: 6.

7. The expression cassette of claim 6, wherein the promoter expresses said polynucleotide in maternal reproductive tissue.

8. The expression cassette of claim 7, wherein the maternal reproductive tissue is selected from the group consisting of spikelet tissue, bract tissue, spikelet meristem tissue, inflorescence stalk tissue, ear node, and immature floral tissue.

9. The expression cassette of claim 6, wherein the promoter is an OsMADS promoter.

10. The expression cassette of claim 9, wherein the OsMADS promoter is an OsMADS 6 promoter.

11. A method for increasing yield in a maize plant, the method comprising:
 a. introducing into a maize plant cell the expression cassette as described in claim 6;
 b. regenerating a maize plant from the maize plant cell of a); and
 c. producing a maize plant with increased yield.

* * * * *